(12) United States Patent
Yoo et al.

(10) Patent No.: US 10,954,348 B2
(45) Date of Patent: Mar. 23, 2021

(54) BIOCOMPATIBLE NANOPARTICLE AND USE THEREOF

(71) Applicant: KYUNGPOOK NATIONAL UNIVERSITY INDUSTRY-ACADEMIC COOPERATION FOUNDATION, Daegu (KR)

(72) Inventors: Jeongsoo Yoo, Daegu (KR); Woonghee Lee, Daegu (KR)

(73) Assignee: Kyungpook National University Industry-Academic Cooperation Foundation, Daegu (KR)

(*) Notice: Subject to any disclaimer, the term of this patent is extended or adjusted under 35 U.S.C. 154(b) by 0 days.

(21) Appl. No.: 16/040,871

(22) Filed: Jul. 20, 2018

(65) Prior Publication Data

US 2018/0327554 A1 Nov. 15, 2018

Related U.S. Application Data

(63) Continuation of application No. PCT/KR2017/000730, filed on Jan. 20, 2017.

(30) Foreign Application Priority Data

Jan. 20, 2016 (KR) ........................ 10-2016-0007104

(51) Int. Cl.

| | |
|---|---|
| *C08J 3/24* | (2006.01) |
| *A61K 9/51* | (2006.01) |
| *A61K 51/06* | (2006.01) |
| *B82Y 5/00* | (2011.01) |
| *C08G 65/30* | (2006.01) |
| *C08B 37/00* | (2006.01) |
| *A61K 47/69* | (2017.01) |
| *A61K 9/06* | (2006.01) |
| *A61K 49/18* | (2006.01) |
| *A61K 51/12* | (2006.01) |
| *C08G 81/00* | (2006.01) |
| *C08B 15/00* | (2006.01) |
| *C08L 71/02* | (2006.01) |
| *C08H 1/00* | (2006.01) |
| *C08B 33/04* | (2006.01) |
| *C08B 37/18* | (2006.01) |
| *C08G 65/34* | (2006.01) |
| *B01J 19/08* | (2006.01) |
| *C07H 3/06* | (2006.01) |
| *C08B 37/16* | (2006.01) |

(Continued)

(52) U.S. Cl.
CPC ............. *C08J 3/246* (2013.01); *A61K 9/06* (2013.01); *A61K 9/5161* (2013.01); *A61K 47/6935* (2017.08); *A61K 47/6939* (2017.08); *A61K 49/1818* (2013.01); *A61K 51/065* (2013.01); *A61K 51/1244* (2013.01); *B01J 19/085* (2013.01); *B82Y 5/00* (2013.01); *C07H 3/06* (2013.01); *C08B 15/00* (2013.01); *C08B 33/04* (2013.01); *C08B 37/003* (2013.01); *C08B 37/0006* (2013.01); *C08B 37/0012* (2013.01); *C08B 37/0021* (2013.01); *C08B 37/0063* (2013.01); *C08B 37/0069* (2013.01); *C08B 37/0072* (2013.01); *C08B 37/0084* (2013.01); *C08B 37/18* (2013.01); *C08G 65/30* (2013.01); *C08G 65/34* (2013.01); *C08G 81/00* (2013.01); *C08H 1/00* (2013.01); *C08L 71/02* (2013.01); *B01J 2219/0877* (2013.01); *B01J 2219/12* (2013.01); *C08G 2270/00* (2013.01); *C08J 2305/00* (2013.01); *C08J 2305/02* (2013.01); *C08J 2305/04* (2013.01); *C08J 2305/08* (2013.01); *C08J 2305/16* (2013.01); *C08J 2471/02* (2013.01)

(58) Field of Classification Search
None
See application file for complete search history.

(56) References Cited

U.S. PATENT DOCUMENTS

| | | | | |
|---|---|---|---|---|
| 2008/0274161 | A1* | 11/2008 | Muratoglu | ............... A61L 27/52 424/425 |
| 2009/0004118 | A1* | 1/2009 | Nie | .................... A61K 49/0002 424/9.35 |

(Continued)

FOREIGN PATENT DOCUMENTS

JP H08301903 A * 11/1996

OTHER PUBLICATIONS

Binh, D., et al., "A study on size effect of carboxymethyl starch nanogel crosslinked by electron beam radiation", Rad. Phys. Chem., 2012, pp. 906-912 (Year: 2012).*

(Continued)

*Primary Examiner* — Michael G. Hartley
*Assistant Examiner* — Lance W Rider
(74) *Attorney, Agent, or Firm* — Levenfeld Pearlstein, LLC

(57) ABSTRACT

The present invention relates to a biocompatible nanoparticle and a use thereof and, more specifically, to a biocompatible nanoparticle formed by irradiation an electron beam to an aqueous solution comprising at least one substance selected from the group consisting of a polysaccharide, a derivative thereof and a polyethylene glycol, thereby inducing inter-molecular cross-linking or intra-molecular cross-linking, and to a use of the biocompatible nanoparticle in a drug carrier, a contrast agent, a diagnostic agent or an intestinal adhesion prevention agent or for disease prevention and treatment.

1 Claim, 24 Drawing Sheets

(51) Int. Cl.
  *C08B 37/02*  (2006.01)
  *C08B 37/08*  (2006.01)

(56) References Cited

U.S. PATENT DOCUMENTS

2012/0107369 A1* 5/2012 Yeoman, III ............ A61K 9/06
                                                          424/400
2014/0199232 A1* 7/2014 Winchurch ............ A61K 47/58
                                                          424/1.11

OTHER PUBLICATIONS

Pasanphan, W., et al. "Systematic fabrication of chitosan nanoparticle by gamma irradiation", Radiation Physics and Chemistry, pp. 1095-1102 (Year: 2010).*
Vo, K.D.N., et al., "Radiation synthesis of chitosan stabilized gold nanoparticlescomparison between e-beam andγirradiation", Radiation Physics and Chemistry, pp. 84-87 (Year: 2014).*
Krsko, P., et al., "Electron-Beam Surface-Patterned Poly(ethylene glycol) Microhydrogels" Langmuir, pp. 5618-5625 (Year: 2003).*
Reichelt, S., et al., "Biocompatible polysaccharide-based cryogels", Materials Science Engineering C, pp. 164-170 (Year: 2014).*
Kovalev, G.V., et al., "Degradation and Crosslinking of Dextran in Aqueous Solutions by /-Radiolysis: The Effect of Hydrogen Ions" Radiation CHemistry, pp. 104-109 (Year: 2000).*
Yoshii, F., et al., "Hydrogels of polysaccharide derivatives crosslinkedwith irradiation at paste-like condition", NIM B, pp. 320-324 (Year: 2003).*
JPH08301903A Translation, accessed from: https://patents.google.com/patent/JPH08301903A/en; accessed on Oct. 22, 2020, pp. (Year: 2020).*
Bae, Ki Yun et al., Oil-Encapsulating PEO-PPO-PEO/PEG Shell Cross-Linked Nanocapsules for Target-Specific Delivery of Paclitaxel, Biomacromolecules, 2007, pp. 650-656, vol. 8, American Chemical Society, Washington D.C.
Choi, Seung Ho et al., Temperature-Sensitive Pluronic/Poly(ethylenimine) Nanocapsules for Thermally Triggered Disruption of Intracellular Endosomal Compartment, Biomacromolecules, 2006, pp. 1864-1870, vol. 7, American Chemical Society, Washington D.C.
Birnbaum, Duane T. et al., Controlled release of beta-estradiol from PLAGA microparticles: The effect of organic phase solvent on encapsulation and release, Journal of Controlled Release, 2000, pp. 375-387, vol. 65, Elsevier, New York City, NY.
Debele, Tilahun Ayane et al., Polysaccharide based nanogels in the drug delivery system: Application as the carrier of pharmaceutical agents, Materials Science and Engineering C, 2016, pp. 964-981, vol. 68, Elsevier, New York City, NY.
Wach, Radoslaw A. et al., Hydroxyl radical-induced crosslinking and radiation-initiated hydrogel formation in dilute aqueous solutions of carboxymethylcellulose, Carbohydrate Polymers, 2014, pp. 412-415, vol. 112, Elsevier, New York City, NY.
Ramnani, S.P. et al., Synthesis and Characterization of Crosslinked Chitosan Formed by gamma Irradiation in the Presence of Carbontetrachloride as a Sensitizer, Journal of Polymer Science, 2004, pp. 3897-3909, vol. 42, Wiley Periodicals, Inc., NY.
Al-Assaf, S. et al., Application of ionizing radiations to produce new polysaccharides and proteins with enhanced functionality, Nuclear Instruments and Methods in Physics Research B, 2007, pp. 37-43, vol. 265, Elsevier, New York City, NY.
Saengthong, S. et al. Fabrication of Microporous Chitosan/Silk Fibroin as a Scaffold Material Using Electron Beam, Macromolecular Research, 2014, pp. 717-724, vol. 22, No. 7, The Polymer Society of Korea, South Korea.
Yamaguchi, N. et al., Polysaccharide-Poly(ethylene glycol) Star Copolymer as a Scaffold for the Production of Bioactive Hydrogels, Biomacromolecules, 2005, pp. 1921-1930, vol. 6, No. 4, Department of Materials Science and Engineering and Delaware Biotechnology Institute, DE.
Hamzah, M. Y. et al., Preparation and Characterization of Polyethylene Glycol Diacrylate Microgels Using Electron Beam Radiation, AIP Conference Proceedings, 2014, pp. 141-144, vol. 1584, No. 141, AIP Publishing LLC, NY.
Dispenza, C. et al., E-beam crosslinked, biocompatible functional hydrogels incorporating polyaniline nanoparticles, Radiation Physics and Chemistry, 2012, pp. 1456-1459, vol. 81, Elsevier, NY.
Liu, Z., Polysaccharides-based nanoparticles as drug delivery systems, Advanced Drug Delivery Reviews, 2008, pp. 1650-1662, vol. 60, Elsevier, NY.
International Search Report issued by ISA/KR in connection with PCT/KR2017/000730 dated Apr. 20, 2017.

* cited by examiner

BIOCOMPATIBLE NANOPARTICLE AND USE THEREOF

TECHNICAL FIELD

This application claims priority from and the benefit of Korean Patent Application No. 10-2016-0007104 filed on 20 Jan. 2016, which is hereby incorporated herein by reference in its entirety.

The present invention relates to biocompatible nanoparticles and uses thereof and, more specifically, to biocompatible nanoparticles formed through inter-molecular crosslinking or intra-molecular crosslinking introduced by electron beam irradiation of an aqueous solution of at least one material selected from the group consisting of polysaccharides, derivatives thereof, and polyethylene glycol, and to a drug delivery system, a contrast agent, a diagnostic agent, or an adhesion barrier using the biocompatible nanoparticles, and to uses of the biocompatible nanoparticles for the prevention and treatment of diseases.

BACKGROUND ART

Techniques for effectively and rapidly preparing very small particles with uniform sizes have been constantly required in various industrial fields. Such small particles with uniform sizes have many advantages, particularly among which good flowability and little deviation in inter-particle interaction are very advantageous in industrial applications. For example, in medicinal industries, the particle size of a therapeutic agent is a very important factor in the degradation rate, biological ability, formulation, and the like, and thus as the deviation in the interaction between the particles of a therapeutic agent becomes smaller, the overall stability of the therapeutic agent becomes better.

In medicinal products, nano-sized particles of a therapeutic agent have the following advantages. First, as for a drug having a small intestinal absorption rate in oral administration, more nanoparticles can be absorbed compared with large-sized particles, and thus the bioavailability of the therapeutic agent can be increased. Furthermore, the dosage form of a therapeutic agent can be varied, for example, as a drug that has been administered only via oral route can be administered into patients by inhalation. In addition, the release rate of a therapeutic agent is a very important factor in the dosage form of a controlled-release therapeutic agent, and thus, when the particle size of a therapeutic agent is made on a nano scale, the particle size becomes relatively more uniform, thus the release rate of the therapeutic agent can be expected, thereby making it possible to produce a more effective therapeutic agent.

As described above, uniform nanoparticles have various advantages, and thus various attempts have been made to prepare an active material in a nanoparticle form. For example, Hirokawa, Takashi et al. in WO 2008/126797 suggested a process of obtaining a nano-scale active material by mixing sodium chloride and a polyol compound with an active material and then wet-milling the mixture without grinding media. This process has a disadvantage in that, due to the use of excessive sodium chloride and polyol compounds, a process of removing sodium chloride and polyol compounds needs to be essentially conducted in order to use the obtained nanoparticles as medicinal products. U.S. Pat. No. 5,202,129 discloses a method for producing fine particles of a poorly water-soluble drug by mixing the poorly water-soluble drug with 2.5 times or more of low-molecular weight sugar or sugar-alcohol and then dry-grinding the mixture. However, this method has a disadvantage in that, due to the use of excessive sugar, it is necessary to disperse the ground mixture in water and then filter the dispersion to remove sugar, followed by again drying, in order to actually use the fine particles in medicinal products. US Patent Publication No. 2004/0067251 A1 discloses a method for manufacturing particles by dissolving an active material in an organic solvent and spraying the resulting solution into an aqueous solution containing a surfactant dissolved therein.

In addition, most nanoparticles used to deliver therapeutic proteins or drugs in vivo are manufactured through an emulsion evaporation method using an organic solvent, so the manufacturing process including from preparing to drying is complicated and time-consuming, the cost increases due to the use of the organic solvent, and a problem due to the use of the organic solvent may be caused in vivo (T. G. Park, et al., Biomacromolecules 8 (2007) 650-656; T. G. Park, et al., Biomacromolecules 7 (2006) 1864-1870; D. T. Birnbaum, et al., J. Control. Rel. 65 (2000) 375-387).

A hydrogel is a polymer with a three-dimensional network structure in which the polymer is crosslinked, and has a swelling property to absorb a fluid from the outside. Therefore, a hydrogel, like biological tissue, can contain a large amount of moisture or bio-fluid, and is smoother and has excellent biocompatibility compared with other synthetic materials, and thus has been widely studied in medical and pharmaceutical fields. Such a hydrogel has been generally manufactured by a method wherein a chemical material, such as a crosslinking agent and/or a curing agent, is added to a polymer material. However, the crosslinking agent and/or curing agent itself used in the crosslinking reaction is harmful to the biological body, and thus a hydrogel manufactured by using such a crosslinking agent and/or a curing agent may cause a harmful action when used in the biological body. Especially, such a hydrogel is not suitable for use as a medical and pharmaceutical material, such as wound dressings, drug delivery carriers, contact lenses, cartilage, and adhesion barriers.

In addition, when a crosslinking agent and/or a curing agent is used, the residual crosslinking agent and/or curing agent in the hydrogel after the preparation of the hydrogel needs to be collected, and thus the preparation process is complicated and the cost therefor is increased. Therefore, continuous efforts have been conducted to produce nanometer-sized, polymer-derived hydrogels without the use of a crosslinking agent and/or a curing agent, and as a result of these efforts, it has been reported that nanometer-sized hydrogels are produced by exposure of a synthetic polymer to radiation.

However, since the synthetic polymer-derived nanohydrogels are not suitable for medical use in terms of biocompatibility and biodegradability, there is a need of development of nanoparticles that are formed only by intra-molecular or inter-molecular crosslinking of polysaccharides or oligosaccharides, without the use of a crosslinking agent, a curing agent, an organic solvent, or the like.

DETAILED DESCRIPTION OF THE INVENTION

Technical Problem

The present inventors found that pure biocompatible nanoparticles composed of only inter-molecular or intra-molecular crosslinking of at least one selected from the group consisting of polysaccharides, derivatives thereof, and polyethylene glycol (PEG) can be produced by manufacturing nanoparticles using only an electron beam without the use of any artificial crosslinking agent or organic solvent, other than a polysaccharide, a derivative thereof, or PEG, and thus completed the present invention.

Therefore, an aspect of the present invention is to provide a biocompatible nanoparticle formed exclusively by inter-molecular crosslinking or intra-molecular crosslinking of at least one selected from the group consisting of polysaccharides, derivatives thereof, and PEG.

Another aspect of the present invention is to provide a drug delivery system in which at least one selected from the group consisting of nucleic acids, proteins, polysaccharides, and drugs is conjugated to the biocompatible nanoparticle.

Another aspect of the present invention is to provide a pharmaceutical composition containing the drug delivery system as an active ingredient.

Another aspect of the present invention is to provide a contrast agent composition containing a nanoparticle and a pharmaceutically acceptable carrier or additive, the nanoparticle being labeled with at least one label material selected from the group consisting of radioactive isotopes, organic fluorescent dyes, quantum dots as inorganic materials, magnetic resonance imaging (MRI) contrast agents, computed tomography (CT) contrast agents, positron emission tomography (PET) contrast agents, ultrasound contrast agents, and fluorescent contrast agents.

Another aspect of the present invention is to provide a method for preparing a biocompatible nanoparticle, the method comprising: (a) adding, to water, at least one material selected from the group consisting of polysaccharides, derivatives thereof, and polyethylene glycol to prepare a solution; and (b) irradiating the solution prepared in step (a) with an electron beam to crosslink the material.

Technical Solution

In accordance with an aspect of the present invention, there is provided a biocompatible nanoparticle formed exclusively by inter-molecular crosslinking or intra-molecular crosslinking of at least one selected from the group consisting of polysaccharides, derivatives thereof, and PEG.

In accordance with another aspect of the present invention, there is provided a drug delivery system in which at least one selected from the group consisting of nucleic acids, proteins, polysaccharides, and drugs is conjugated to the biocompatible nanoparticle.

In accordance with another aspect of the present invention, there is provided a pharmaceutical composition containing the drug delivery system as an active ingredient.

In accordance with another aspect of the present invention, there is provided a contrast agent composition containing a nanoparticle and a pharmaceutically acceptable carrier or additive, the nanoparticle being labeled with at least one label material selected from the group consisting of radioactive isotopes, organic fluorescent dyes, quantum dots as inorganic materials, magnetic resonance imaging (MRI) contrast agents, computed tomography (CT) contrast agents, positron emission tomography (PET) contrast agents, ultrasound contrast agents, and fluorescent contrast agents.

In accordance with another aspect of the present invention, there is provided a method for preparing a biocompatible nanoparticle, the method comprising: (a) adding, to water, at least one material selected from the group consisting of polysaccharides, derivatives thereof, and polyethylene glycol to prepare a solution; and (b) irradiating the solution prepared in step (a) with an electron beam to crosslink the material.

Hereinafter, the present invention will be described in detail.

The present invention provides a biocompatible nanoparticle formed exclusively by inter-molecular crosslinking or intra-molecular crosslinking of at least one selected from the group consisting of polysaccharides, derivatives thereof, and PEG.

As used herein, the term nanoparticle refers to a particle having a size of several to several hundred nanometers (nm, 1 billionth of a meter). Preferably, in the present invention, the nanoparticle may be characterized by having a particle size of 1-700 nm, but are not limited thereto, and the shape of the nanoparticle may be spherical, but is not limited thereto. In the present invention, the nanoparticle has a concept encompassing a nanogel or a nanohydrogel, and hereinafter, a nanoparticle, a nanogel, or a nanohydrogel are all used to mean the nanoparticle according to the present invention.

All medical materials in addition to polymer materials necessarily require biocompatibility, and such biocompatibility may have two different meanings. The biocompatibility in a broad sense denotes having desired functions and the safety with respect to living bodies, and the biocompatibility in a narrow sense denotes the biological safety with respect to living bodies, that is, being non-toxic and sterilizable. Therefore, in the present invention, the biocompatible nanoparticle may refer to a nanoparticle that exerts desired functions in living bodies, has no toxicity of materials per se, and can be sterilized.

In the present invention, the polysaccharides or derivatives thereof, which are raw materials of biocompatible nanoparticles, are not only highly usable as carriers for drugs or the like due to multifunctional groups present in chemical structures thereof, but also have excellent usability compared with synthetic polymers in medicinal and pharmaceutical fields due to physical and chemical characteristics thereof, such as biocompatibility and biodegradability (Materials Science and Engineering C 68 (2016) 964.981).

As used herein, the term polysaccharides means large molecules in which three or more monosaccharides form a consecutive chain through glycoside linkages. The polysaccharides of the present invention include oligosaccharides in which a small amount of monosaccharides are condensed. The polysaccharides react with other compounds to easily produce derivatives thereof since a very reactive hydroxyl group, amino group, carboxylic acid group, or the like are present in the structures of the polysaccharides. The derivatives of the present invention include derivatives in which alkyl, alkenyl, carboxymethyl, hydroxyalkyl, acetyl, or the like is linked to such functional groups present in the polysaccharides, and the kind of derivatives is not particularly limited.

In the present invention, the polysaccharides may fundamentally exhibit water solubility such that the polysaccharides are dissolved in water, and even if insoluble, the polysaccharides are dissolved in water by derivatization, for example, hydroxyalkylation, alkylation, carboxyalkylation, or the like. In the present invention, the polysaccharides may be chitosan, gelatin, collagen, mannan, dextran sulfate, α-cyclodextrin, β-cyclodextrin, γ-cyclodextrin, fructo-oligosaccharides, isomalto-oligosaccharides, inulin, hyaluronic acid, alginate, glycogen, amylose, carboxymethyl dextran, beta-glucan, hydroxyethyl cellulose, carboxymethyl cellulose, fucoidan, or chondroitin, but are not limited thereto.

That is, in the present invention, the biocompatible nanoparticles are formed by only inter-molecular crosslinking or intra-molecular crosslinking of polysaccharides or derivatives thereof, and thus contain no foreign materials, which may be incorporated in the manufacturing procedure of nanoparticles, and therefore, the biocompatible nanoparticles can be easily degraded in the body and have no concern about side effects and toxicity due to the accumulation thereof in the body.

Meanwhile, it is common to use a crosslinking agent to induce crosslinking of polymers in view of the production of nanoparticles or nanogels using polymers. In the case of inducing crosslinking of polymers using a crosslinking agent, the crosslinking agent mediates inter-polymer linking or intra-polymer linking and thus may be incorporated into nanoparticles. Because of a high concentration of the crosslinking agent, the crosslinking agent may remain in an active state in reaction mixture after reactions. Therefore, a purification procedure is essentially conducted during nanoparticle manufacturing processes. In addition, the crosslinking agent remaining in the nanoparticles may cause various side effects after administration into the body. However, the present inventors confirmed that nanometer-sized hydrogels were formed by irradiating polysaccharides with an electron beam under particular conditions to induce inter-molecular or intra-molecular crosslinking of the polysaccharides. The nanoparticles, which are formed by only the linking of the polysaccharide itself without containing foreign substances, such as a crosslinking agent or a metal cation inside the molecules, have not been reported as ever, and the present inventors have revealed for the first time such nanoparticles through the present invention.

Since the biocompatible nanoparticles of the present invention are formed only by inter-molecular or intra-molecular crosslinking of the polysaccharide itself, there are no problems described above of the nanoparticles produced by the conventional method. Moreover, since the nanoparticles of the present invention can be produced by electron beam irradiation in an aqueous solution state without using any organic solvent, contaminations or complicated processes that may occur during the production procedure are not generated, and thus the nanoparticles of the present invention are industrially highly applicable.

According to an example of the present invention, the present inventors produced nanometer-sized particles by electron beam irradiation of an aqueous solution of hyaluronic acid, mannan, β-cyclodextrin, alginate, a fructo-oligosaccharide, an isomalto-oligosaccharide, fucoidan, chitosan, or carboxymethyl-dextran.

According to another example of the present invention, it was confirmed that nanoparticles were formed by irradiating an aqueous solution of carboxymethyl-dextran or polyethylene glycol with an electron beam, and it was also confirmed that desired nanoparticles were favorably formed even when a mixed aqueous solution of carboxymethyl-dextran and polyethylene glycol was irradiated with an electron beam.

That is, the biocompatible nanoparticles of the present invention may be composite nanoparticles of at least one polysaccharide and polyethylene glycol. The term "polyethylene glycol (PEG)" used herein is a polymer material that is introduced to improve the blood residence time of nanoparticles by increasing hydrophilicity of the nanoparticle surface and preventing the fast degradation caused by immune functions in the human body. Such modification with polyethylene glycol is called PEGylation. PEGylation can produce polymer nanoparticles with reduced hepatic accumulation and increased blood retention time. That is, the introduction of polyethylene glycol onto the nanoparticle surface can increase the hydrophilicity of particles, can prevent fast degradation in the body by preventing the recognition from immune functions, including macrophages and the like, in the human body, which engulf and digest pathogenic bacteria, wastes, and externally inflow substances, so called stealth effect, and can increase the blood retention time of nanoparticles. The present inventors confirmed that a polysaccharide molecule and a polyethylene glycol molecule form inter-molecular crosslinking by electron beam irradiation of a mixed aqueous solution of a polysaccharide and polyethylene glycol even without conducting separate PEGylation, thereby producing nanoparticles. Herein, the polyethylene glycol has a molecular weight of preferably 100-150,000 Da, and may have various structures, such as linear or branched form.

As above, the biocompatible nanoparticles of the present invention may preferably be as follows:

(i) nanoparticles formed by only inter-molecular or intra-molecular crosslinking of a polysaccharide or a derivative thereof; and (ii) nanoparticles produced by inter-molecular crosslinking of polyethylene glycol with a polysaccharide or derivative thereof.

In the present invention, the nanoparticles may be prepared by the following method comprising the following steps:

(a) adding, to water, at least one material selected from the group consisting of a polysaccharide, a derivative thereof, and polyethylene glycol to prepare a solution; and (b) irradiating the solution prepared in step (a) with an electron beam to crosslink the material.

(a) adding, to water, at least one material selected from the group consisting of polysaccharides, derivatives thereof, and polyethylene glycol to prepare a solution Since most nanoparticles used to deliver therapeutic proteins or drugs in vivo are manufactured through an emulsion evaporation method using an organic solvent, the manufacturing process from preparing to drying is complicated and time-consuming, the cost due to the use of the organic solvent may be increased, and a problem due to the use of the organic solvent may be caused in vivo (T. G. Park, et al., Biomacromolecules 8 (2007) 650-656; T. G. Park, et al., Biomacromolecules 7 (2006) 1864-1870; D. T. Birnbaum, et al., J. Control. Rel. 65 (2000) 375-387).

However, in the manufacturing procedure of the nanoparticles of the present invention, only water is used as a solvent without the use of an organic solvent, so there is no fear of various side effects due to the remaining of an organic solvent, and the manufacturing procedure does not include a purification process, which is to be conducted to remove an organic solvent, so the nanoparticle synthesis process can be simplified and the production efficiency can be increased.

In the present invention, the molecular weight of a polysaccharide or a derivative thereof is not particularly limited, but may preferably be 5-3000 kDa.

The concentration of an aqueous solution of a polysaccharide or derivative thereof, which is used to manufacture the nanoparticles of the present invention, may be 0.1-15% (w/v). According to an example of the present invention, it could be seen that the specific concentrations of aqueous solution for forming nanoparticles were not identical in different kinds of polysaccharides, but nanoparticles were formed within a range of 0.1-15% (w/v).

If the concentration of a polysaccharide aqueous solution is less than 0.1%, inter-molecular crosslinking is not easy to form, and thus nanoparticles may not be formed, and the formed nanoparticles may not have a uniform size. If more than 15%, inter-molecular crosslinking excessively occurs, resulting in bulk gels, and thus nanoparticles may not be produced, and in the case where a polymer aqueous solution is prepared, there is an inconvenience that polymers need to be dissolved with heat applied. Therefore, less than 0.1% and more than 15% are not preferable for a polysaccharide aqueous solution.

More preferably, in the present invention, the concentration of the polysaccharide aqueous solution may be 0.1-10%.

Still more preferably, the concentration is:
(1) 0.5-7%, and most preferably 1-5% for hyaluronic acid;
(2) 0.5-7%, and most preferably 0.5-3% for mannan;
(3) 0.5-3%, and most preferably 1-3% for β-cyclodextrin;
(4) 0.5-10%, and most preferably 0.5-7% for alginate;
(5) 0.5-10%, and most preferably 0.5-3% for fructo-oligosaccharide;
(6) 3-10%, and most preferably 3-7% for isomalto-oligosaccharide;
(7) 0.1-3%, and most preferably 0.3-1% for chitosan;
(8) 0.5-3% for fucoidan; and
(9) 3-10%, and most preferably 5-10% for carboxymethyl-dextran.

(b) irradiating the solution generated in step (a) with an electron beam to crosslink the material As described above, the present invention never uses an initiator, such as a crosslinking agent, to manufacture biocompatible nanoparticles, and uses an electron beam to induce inter-molecular or intra-molecular crosslinking of a polysaccharide or a derivative thereof.

The technique of inducing crosslinking using an electron beam does not require a harmful catalyst or the like compared with reactions by other general chemical additives, and thus the technique is a clean means and enables short-time treatment, leading to small energy consumption and simplified manufacturing processes.

When the polymer material is irradiated by radiation, such as an electron beam, covalent linkages present in the polymer material are broken to form radicals containing non-covalent electron pairs, and such radicals irregularly interact with each other. Depending on the relative rate of breakage and recombination of inter-molecular covalent linkages, crosslinking may be formed or the polymer material may be degraded into low-molecular weight fractions. The effect of the electron beam irradiation on the polymer material is determined by the structure of the polymer material.

Specifically, according to Radoslaw A. Wach et al. (Carbohydrate Polymers 112 (2014) 412-415), a radiation method of inducing crosslinking of a polymer material by radiation exposure are well applied to synthetic polymers, whereas the exposure of a polysaccharide to radiation merely generates materials with reduced molecular weights through the induction of molecular breakage, but not form crosslinkage. In order to solve these problems and achieve crosslinking of a polysaccharide using a radiation method, a technique of using an additive for promoting crosslinking reactions, such as alkyne gas or carbon tetrachloride, has been designed (Journal of Polymer Science Part A: Polymer Chemistry, 42, 3897?3909. Nuclear Instruments and Methods in Physics Research Section B, 265, 37?43), or a technique of adjusting the pH of a solution to induce crosslinking has been attempted (Carbohydrate Polymers 112 (2014) 412?415). However, even if crosslinking of a polysaccharide is induced according to the previously reported methods, there is no example of generation of nanometer-sized particles.

Meanwhile, the degree of crosslinking induced by electron beam irradiation of a polysaccharide or a derivative thereof is varied depending on the experimental condition during the electron beam irradiation. That is, the size, uniformity, and the like of the particles are varied depending on the concentration and temperature of the polysaccharide aqueous solution irradiated with the electron beam, the dose of the electron beam, and the like.

In the present invention, the energy intensity of the irradiated electron beam may be 5-250 kGy and preferably 10-250 kGy, but is not limited thereto. The energy intensity of the electron beam can be properly adjusted and selected by a person skilled in the art according to the size of nanoparticles to be produced, considering the concentration of the polysaccharide aqueous solution, the kind of polysaccharide, and the like.

Still more preferably, the concentration is:
(1) 30-230 kGy for hyaluronic acid;
(2) 30-230 kGy for mannan;
(3) 10-100 kGy, and most preferably 30-70 kGy for β-cyclodextrin;
(4) 10-230 kGy for alginate;
(5) 10-230 kGy, and most preferably 150-230 kGy for fructo-oligosaccharide;
(6) 10-230 kGy, and most preferably 30-70 kGy for isomalto-oligosaccharide;
(7) 100-230 kGy, and most preferably 150-230 kGy for fucoidan;
(8) 10-230 kGy, and most preferably 150-230 kGy for chitosan; and
(7) 100-230 kGy, and most preferably 150-230 kGy for carboxymethyl-dextran.

In the present invention, the irradiation time of the electron beam may be 1 sec to 2 hrs. In the present invention, a linear electron beam accelerator was used as an electron beam irradiation device for producing nanoparticles. An electron beam with doses of 5 kGy, 10 kGy, 50 kGy, 100 kGy, and 200 kGy was irradiated on a polysaccharide aqueous solution on a conveyor moving at a predetermined rate such that electron beam irradiation conditions are controlled in a manner of adjusting the beam current and the irradiation time. The irradiation time and beam current of the electron beam can be properly adjusted and selected by a person skilled in the art according to the size of nanoparticles to be produced, considering the concentration of a sample, the energy intensity of an electron beam to be irradiated, and the like.

Also, the present invention can manufacture nanoparticles by further comprising (c), after step (b), adding at least one selected from the group consisting of nucleic acids, proteins, polysaccharides, radioactive substances, and drugs, to the solution containing the biocompatible polymer nanoparticles in step (b).

The nanoparticles manufactured according to the above method may exert effects thereof as a drug delivery system or a contrast agent since a nucleic acid, a protein, a polysaccharide, a radioactive substance, or a drug is encapsulated in the nanoparticle.

Therefore, the present invention provides a drug delivery system in which at least one selected from the group consisting of nucleic acids, proteins, polysaccharides, radioactive substances, and drugs is encapsulated in the nanoparticle.

One of the ideal methods of accurately delivering a drug to the body is to deliver the drug directly to a specific site, such as an affected area. The target sites for drug delivery may be organs, such as heart, kidney, and liver, in the body; tissues, such as muscles, bones, and cartilage; and specific cell units, such as cancer cells. The delivery of the drug only to the diseased site can increase the efficiency of the administered drug and can prevent the delivery of the drug to other sites without diseases, thereby reducing side effects. Due to these advantages, research on drug delivery systems has been actively conducted in the field of materials. The research has been more activated with the development of, specifically, nanotechnology.

As used herein, the term "drug delivery system" refers to a drug delivery system that includes the sustained release of a drug over a long period of time as well as the concepts of predictability and regeneration. Therefore, in the present invention, a drug loaded in the drug delivery system can be released at a rate at which the drug can be uniformly regenerated at a scheduled site over a scheduled time. In the case where the drug is too quickly lost out of the body due to the low bioavailability or very high absorption thereof, such a controlled type drug delivery system can maintain the blood drug concentration at a treatment area for a long time by controlling the release rate of a drug. The drug release regulation mechanism of such an agent employs diffusion, dissolution, osmosis, or ion exchange, which are used in combination in most cases.

Since the biocompatible nanoparticles of the present invention are less toxic in the human body and have excellent water solubility, the biocompatible nanoparticles can effectively deliver a drug to a desired site, and can be utilized as a sustained-release drug delivery system that controls the release rate of a drug by combination with various pharmaceutical techniques. In addition, the fusion of an antibody recognizing a particular antigen or a peptide acting as a ligand to a particular receptor to the nanoparticles of the present invention can also be utilized as a target-specific drug delivery system.

The kind of material that can be encapsulated in the nanoparticle of the present invention is not particularly limited, and may be preferably a nucleic acid, protein, polysaccharide, or drug.

In the present invention, the drug may be at least one selected from the group consisting of antibiotic agents, anticancer drugs, pain relievers, anti-inflammatory agents, antitussive agents, expectorants, sedative agents, muscle relaxants, antiepileptic agents, anti-ulcer agents, antidepressants, antiallergic agents, cardiotonic agent, antiarrhythmic agents, vasodilators, hypertensive diuretic agents, antidiabetic agents, anticoagulants, hemostatic agents, anti-nodule agents, hormone drugs, and combinations thereof, but is not limited thereto.

In addition, diagnostic markers, such as radioactive isotopes, organic fluorescent dyes, quantum dots as inorganic materials, magnetic resonance imaging (MRI) contrast agents, computed tomography (CT) contrast agents, positron emission tomography (PET) contrast agents, ultrasound contrast agents, and fluorescent contrast agents, may be further conjugated to the drug delivery system of the present invention. Therefore, the drug encapsulated in the nanoparticles and the diagnostic marker further conjugated thereto can exert the effects thereof, thereby simultaneously performing therapy and diagnosis of a disease.

According to an example of the present invention, the combination of doxorubicin, which is widely used as an anticancer drug, with a carboxymethyl-dextran nanoparticle, showed an excellent drug loading rate so that the encapsulation efficiency reached about 79%. According to another example of the present invention, the combination of doxorubicin with polyethylene glycol and carboxymethyl-dextran mixed nanoparticle confirmed a very excellent encapsulation efficiency of about 72%, indicating that the nanoparticles of the present invention can be very favorably used as a drug delivery system.

The present invention provides a pharmaceutical composition containing the drug delivery system as an active ingredient.

The therapeutic use of the pharmaceutical composition can be selectively applied depending on the kind of a drug encapsulated in the nanoparticle. That is, the pharmaceutical composition of the present invention can be utilized, depending on the type of the drug encapsulated in the biocompatible polymer, as a composition for the prevention and treatment of a bacterial infection, a composition for the prevention and treatment of cancer, a composition for the prevention and treatment of pain, a composition for the prevention and treatment of an inflammatory disease, a composition for the prevention and treatment of an interstitial disease, a composition for the prevention and treatment of ulcer, a composition for the prevention and treatment of depression, a composition for the prevention and treatment of an allergic disease, a composition for the prevention and treatment of arrhythmia, a composition for the prevention and treatment of hypertension, a composition for the prevention and treatment of diabetes, or a composition for the prevention and treatment of a heart disease.

According to an example of the present invention, it was confirmed that an animal model administered with a pharmaceutical composition containing, as an active ingredient, a polyethylene glycol and carboxymethyl-dextran mixed nanoparticle conjugated to doxorubicin further inhibited tumor growth compared with an animal group administered with free doxorubicin. That is, the pharmaceutical composition containing the drug delivery system of the present invention as an active ingredient exhibits an effect of preventing a drug from being easily degraded in the body and excreted out of the body or an effect of achieving the sustained-release of a drug at a desired site, and thus it is considered that the pharmaceutical composition of the present invention can show more excellent pharmaceutical activity compared with free drugs.

The pharmaceutical composition of the present invention may further contain a pharmaceutically acceptable additive in addition to a drug delivery system encapsulating a drug. Examples of the pharmaceutically acceptable additive may include starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxymethyl starch, carnauba wax, synthetic aluminum silicate, stearic acid, magnesium stearate, aluminum stearate, calcium stearate, white sugar, dextrose, sorbitol, and talc. The pharmaceutically acceptable additive according to the present invention is preferably contained in 0.1-90 parts by weight relative to the pharmaceutical composition, but is not limited thereto.

In addition, the composition of the present invention may be administered in several oral and parental dosage forms in the actual clinical administration, and may be formulated by using a diluent or excipient, such as a filler, an extender, a binder, a wetting agent, a disintegrant, or a surfactant, of which are generally used.

Solid preparations for oral administration may include a tablet, a pill, a powder, a granule, a capsule, and the like. These solid preparations may be prepared by mixing at least one excipient, such as starch, calcium carbonate, sucrose, lactose, or gelatin, with a drug delivery system in which a drug is encapsulated in the biocompatible polymer nanoparticle. In addition to such a simple excipient, lubricants, such as magnesium stearate and talc, may be used. Liquid preparations for oral administration correspond to a suspension, a liquid for internal use, oil, syrup, and the like, and may include several types of excipient, for example, a wetting agent, a sweetener, an aroma, a preservative, and the like, in addition to simple diluents that are frequently used, such as water and liquid paraffin.

Preparations for parenteral administration may include a sterile aqueous solution, a non-aqueous solvent, a suspension, an emulsion, a freeze-dried preparation, and a suppository. The non-aqueous solvent and the suspension solvent may include propylene glycol, polyethylene glycol, vegetable oil such as olive oil, an injectable ester such as ethylolate, and the like. As a substrate for the suppository, Witepsol, Macrogol, twin 61, cacao butter, laurin butter, or glycerogelatin may be used.

Meanwhile, the injection may contain conventional additives, such as a solubilizer, an isotonic agent, a suspending agent, an emulsifier, a stabilizer, and a preservative.

The dose of the pharmaceutical composition of the present invention with respect to the human body may vary depending on patient's age, body weight, and gender, the form of administration, state of health, and severity of disease. The dose may be generally 0.01-100 mg/kg/day, preferably 0.1-20 mg/kg/day, and more preferably 5-10 mg/kg/day. The composition may also be divisionally administered at predetermined intervals according to the determination of a doctor or pharmacist.

The present invention also provides a contrast agent composition containing a nanoparticle and a pharmaceutically acceptable carrier or additive, the nanoparticle being labeled with at least one label material selected from the group consisting of radioactive isotopes, organic fluorescent dyes, quantum dots as inorganic materials, magnetic resonance imaging (MRI) contrast agents, computed tomography (CT) contrast agents, positron emission tomography (PET) contrast agents, ultrasound contrast agents, and fluorescent contrast agents.

Various label materials that can be used for image diagnosis may be attached to the nanoparticles of the present invention, and the nanoparticles may be utilized as a contrast agent composition.

In the present invention, the label material that can be conjugated to the biocompatible nanomaterial may include radioactive isotopes, organic fluorescent dyes, quantum dots as inorganic materials, magnetic resonance imaging (MRI) contrast agents, computed tomography (CT) contrast agents, positron emission tomography (PET) contrast agents, ultrasound contrast agents, and fluorescent contrast agents, but is not limited thereto.

In the use of radioactive isotopes, examples of the radioactive isotopes may include nuclides for single photon emission computed tomography, such as $^{99m}Tc$, $^{123}I$, $^{111}In$, $^{67}Ga$, $^{177}Lu$, $^{201}Tl$, $^{117m}Sn$, and $^{125}I$; nucleotides for positron emission tomography, such as $^{11}C$, $^{13}N$, $^{15}O$, $^{18}F$, $^{38}K$, $^{62}Cu$, $^{64}Cu$, $^{68}Ga$, $^{82}Rb$, $^{124}I$, and $^{89}Zr$; and nucleotides for therapy, such as $^{131}I$, $^{166}Ho$, $^{188}Re$, $^{67}Cu$, $^{89}Sr$, $^{90}Y$, $^{225}Ac$, $^{213}Bi$, and $^{211}At$. Radioactive isotopes can be replaced with non-radioactive isotopes because of almost similar chemical properties therebetween, and even a small amount of radioactive isotopes can be also detected due to comparatively high emission energy, and therefore, the radioactive isotopes have been used for a long time.

Organic fluorescent dyes are widely used as alternatives to radioactive isotopes. The fluorescent dyes emit lights having unique wavelengths when activated by particular wavelengths. Especially, as the search method is miniaturized, radioactive materials also have a detection limit, requiring a long time for search. In contrast, the fluorescence dyes can emit thousands of photons per molecule under appropriate conditions, and thus the detection at the single molecule level is theoretically possible. In the present invention, the kind of organic fluorescent dyes that can be encapsulated or combined in the biocompatible polymer nanomaterial is understood as a concept encompassing all materials that are being used in the art or will be used in the future.

In addition, quantum dots, which are semiconductor nanomaterials, are composed of CdSe, CdS, ZnS, ZnSe, or the like, and emit lights of different colors depending on the size and type thereof. Since the quantum dots have wider active wavelengths than the organic fluorescent dyes and exhibit narrow emission wavelengths, the number of quantum dots emitting different colors is greater than that of organic fluorescent dyes. Therefore, the quantum dots are recently widely used in order to overcome the disadvantages of organic fluorescent dyes. In the present invention, the quantum dots that can be encapsulated or combined in the biocompatible polymer nanoparticles are understood as a concept encompassing all materials that are being used in the art or will be used in the future.

Specific examples of the magnetic resonance imaging (MRI) contrast agents may include transition metal ions including gadolinium (Gd), manganese (Mn), iron (Fe), copper (Cu) and chromium (Cr); hydrophobic complexes of the transition metal ions, including gadopentetate dimeglumine (Gd-DTPA) and gadoterate meglumine (Gd-DOTA); fluorine-containing compounds including perfluorocarbon and perfluoropropane; iron oxide-based, manganese-based, copper-based, and chromium-based nanoparticles; and compounds in which surfaces of the nanoparticles are modified with hydrophobic materials.

Examples of the computed tomography (CT) contrast agents may include iodinated hydrophobic materials derived from iodinated poppy seed oil; and nanoparticles composed of metal elements including bismuth (Bi), gold (Au), and silver (Ag), but are not limited thereto.

Examples of single photon emission computed tomography contrast agents may include: radioactive isotopes including $^{99m}Tc$, $^{123}I$, $^{111}In$, $^{87}Ga$, $^{177}Lu$, $^{201}Tl$, $^{117m}Sn$, and $^{125}I$; and hydrophobic complexes of the radioactive isotopes, but are not limited thereto.

Examples of the positron emission tomography contrast agents may include: radioactive isotopes including $^{11}C$, $^{13}N$, $^{15}O$, $^{18}F$, $^{38}K$, $^{62}Cu$, $^{64}Cu$, $^{68}Ga$, $^{82}Rb$, $^{124}I$, and $^{89}Zr$; and hydrophobic complexes of the radioactive isotopes, but are not limited thereto.

Examples of contrast agents for therapy may include: radioactive isotopes including $^{131}I$, $^{166}Ho$, $^{188}Re$, $^{67}Cu$, $^{89}Sr$, $^{90}Y$, $^{225}Ac$, $^{213}Bi$, and $^{211}At$; and hydrophobic complexes of the radioactive isotopes, but are not limited thereto.

Specific examples of the ultrasound contrast agents may include perfluoropropan, perfluorohexane, sulfur hexafluoride, perfluoropentane, and decafluorobutane, but are not limited thereto.

Specific examples of the fluorescent contrast agents may include: low-molecular weight fluorescent substances including fluorescein, rhodamine, Nile Red, Cy-3 and Cy-5; hydrophobic materials into which the low-molecular weight fluorescent substances are introduced via covalent linkages; quantum dots composed of an inorganic light emitting semiconductor selected from the group consisting of CdSe, CdS, and CdTe with a size of 5-20 nm and surrounded by a heterogeneous ZnS conjugate; and materials in which surfaces of the quantum dots are modified with hydrophobic materials, but are not limited thereto.

The carrier used in the contrast agent composition according to the present invention includes a carrier and a vehicle, which are ordinarily used in a medical field, and specific examples of the carrier may include ion exchange, alumina, aluminum stearate, lecithin, serum protein (such as, human serum albumin), buffer materials (such as, various phosphates, glycine, sorbic acid, potassium sorbate, and partial glyceride mixtures of saturated vegetable fatty acids), water, salts, or electrolytes (such as, protamine sulfate, disodium hydrogen phosphate, potassium hydrogen phosphate, sodium chloride, and zinc salts), colloidal silica, magnesium trisilicate, polyvinylpyrrolidone, cellulose-based substrates, polyethylene glycol, sodium carboxymethyl cellulose, polyarylate, wax, or wool fat, but are not limited thereto. The contrast agent composition of the present invention may further contain, in addition to the above ingredients, a lubricant, a wetting agent, an emulsifier, a suspending agent, or a preservative.

The contrast agent composition according to the present invention can be prepared as an aqueous solution for parenteral administration. Preferably, a buffer solution, such as Hank's solution, Ringer's solution, or physically buffered saline, may be used. A water-soluble injection suspension may contain a substrate capable of increasing the viscosity of the suspension, such as sodium carboxymethyl cellulose, sorbitol, or dextran.

Another preferred form of the contrast agent composition of the present invention may be in the form of a sterile injectable preparation of an aqueous or oily suspension. Such suspensions may be formulated according to techniques known in the art using suitable a dispersing or wetting agent (for example, Tween 80) and a suspending agent. In addition, the sterile injectable preparation may be a sterile injectable solution or suspension in a non-toxic parenterally acceptable diluent or solvent (for example, a solution in 1,3-butanediol). The vehicle and solvent that can be used include mannitol, water, Ringer's solution and an isotonic sodium chloride solution. In addition, sterile non-volatile oil is conventionally used as a solvent or suspending medium. For this purpose, any less-irritating and non-volatile oil, including synthetic mono- or di-glycerides, may be used.

The contrast agent composition of the present invention may further contain at least one additive selected from: other materials conventionally used as pH adjusters, such as citric acid and sodium citrate; and/or other materials conventionally used as sweeteners, such as aspartame, acesulfame potassium, simple syrup, sodium saccharin, calcium saccharin, and sugar; and/or other materials conventionally used as antifoaming agents, such as silicon resins; and/or other materials conventionally used as preservatives, such as alcohols, phenols, organic acids and salts thereof, organic mercury compounds, and parabens; and/or other materials conventionally used as flavoring agents, such as pineapple aroma, strawberry aroma, orange aroma, lemon aroma, chocolate aroma, cola aroma, grape aroma, and pine aroma.

Advantageous Effects

The biocompatible nanoparticles of the present invention are prepared by inducing inter-molecular or intra-molecular crosslinking of a polysaccharide or a derivative thereof through an electron beam, so that there is no a concern of occurrence of toxic problems in the human body caused by the incorporation of an organic solvent or a crosslinking agent; and a separate purification process is not needed during the manufacturing procedure of the nanoparticles, and thus, the nanoparticles can be massively produced by merely electron beam irradiation for a short time, and thus the biocompatible nanoparticles of the present invention are excellent in an aspect of productivity. Furthermore, the nanoparticles of the present invention are very useful in that the nanoparticles can be utilized in various fields, such as a drug delivery system, a pharmaceutical composition, a contrast agent composition, or an adhesion barrier.

MODE FOR CARRYING OUT THE INVENTION

Hereinafter, the present invention will be described in detail.

However, the following examples are merely for illustrating the present invention, and are not intended to limit the scope of the present invention.

Example 1

Conditions for Electron Beam Irradiation Using Electron Beam Accelerator and Preparation Therefor Experiments were conducted by applying an electron beam with various dose conditions to a solution to be irradiated. In the experiments, a linear electron beam accelerator was used, and an electron beam with doses of 5 kGy, 10 kGy, 50 kGy, 100 kGy, and 200 kGy was applied to a sample on a conveyor moving at a predetermined rate in a manner of adjusting the electron beam and the irradiation time. The irradiation time of the electron beam and the irradiation dose thereof can be properly adjusted and selected by a person skilled in the art according to the size of nanoparticles to be produced, in consideration of the temperature condition at the time of electron beam irradiation, the sample concentration, the energy intensity of an electron beam to be irradiated, and the like.

Example 2

Preparation of Nanoparticles by Electron Beam Irradiation 2-1. Carboxymethyl-Dextran Solution and Electron Beam Irradiation Conditions Nanoparticle synthesis experiments were conducted using carboxymethyl-dextran. Electron beams were applied to samples to be irradiated by using a linear electron beam accelerator while the electron beam irradiation conditions were varied in a manner of adjusting the beam current and irradiation time.

More specifically, carboxymethyl-dextran (molecular weight: 10 kDa) was dissolved in water to prepare solutions with concentrations of 0.1%, 0.5%, 1%, 5%, 10%, and 20% (w/v), and the experiments were conducted while the electron beam irradiation energy dose with respect to the carboxymethyl-dextran solutions was varied to 5 kGy, 10 kGy, 50 kGy, 100 kGy, and 200 kGy. Any additive, such as an organic solvent, a crosslinking agent, or an inorganic material, was not added to the prepared carboxymethyl-dextran solutions.

Figure 1:
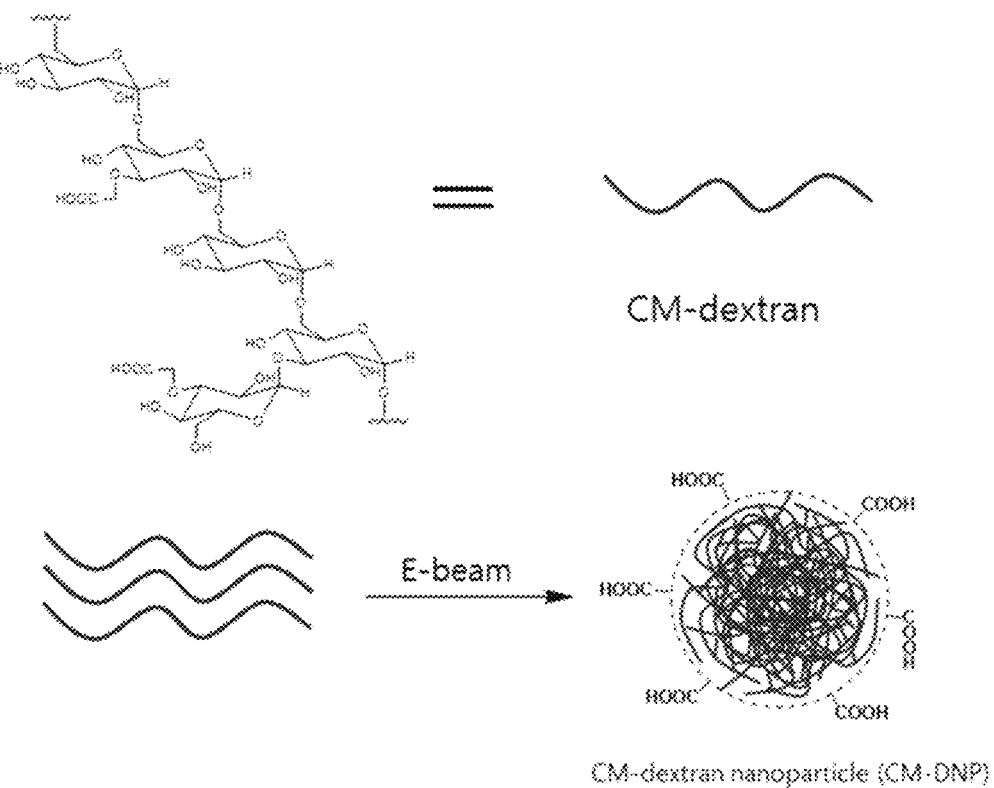
FIG. 1 is a schematic diagram showing a method for manufacturing nanoparticles by irradiating a carboxymethyl-dextran aqueous solution with an electron beam.
Figure 2:
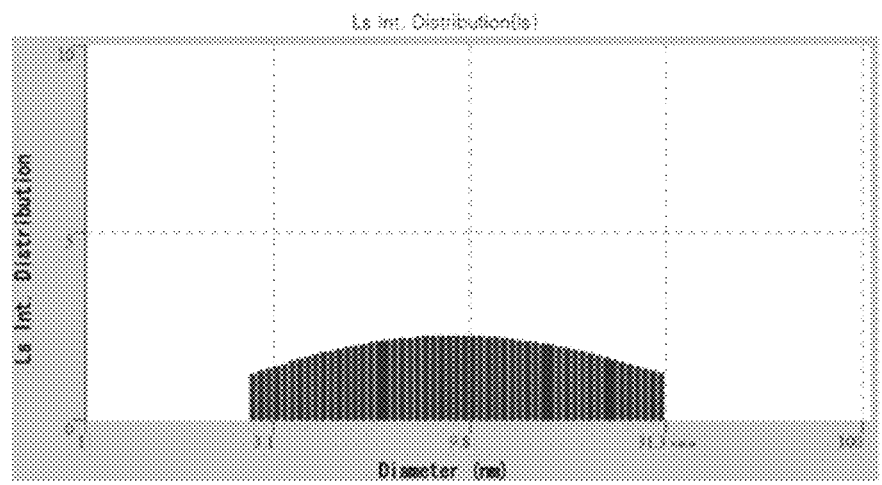
FIG. 2 illustrates DLS results and TEM image of the nanoparticles generated when a 10% carboxymethyl-dextran aqueous solution was irradiated with an electron beam of 200 kGy.
Figure 2:
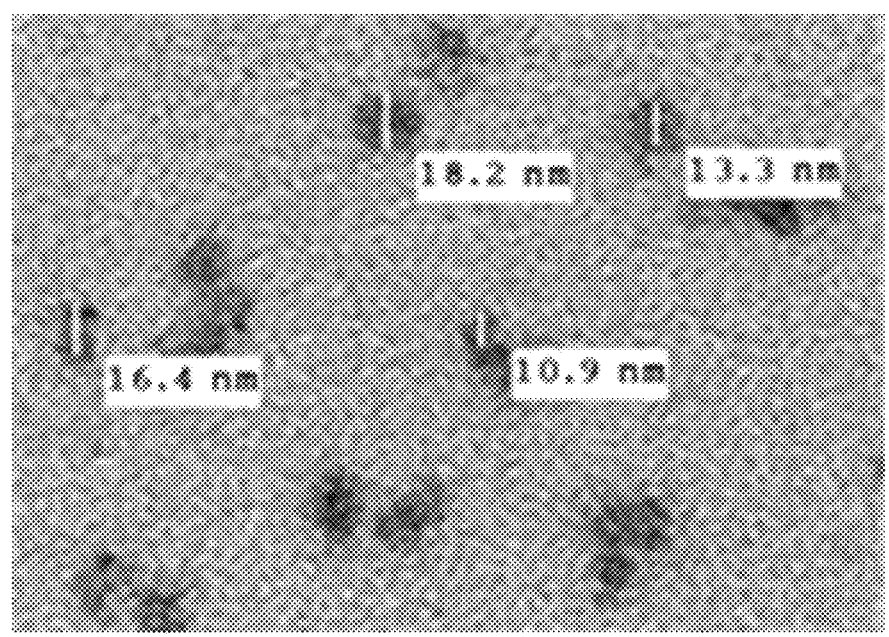

2-2. Preparation of Carboxymethyl-Dextran Nanoparticles by Electron Beam Irradiation Experiments were conducted at various concentrations and various electron beam dose conditions, and as a result of confirming particle sizes of the prepared nanogels through dynamic light scattering (DLS), it could be confirmed that nanoparticles with a uniform size of about 10 nm were synthesized only when an electron beam of 200 kGy was applied to a 10% carboxymethyl dextran solution (FIG. 2).

Figure 3:
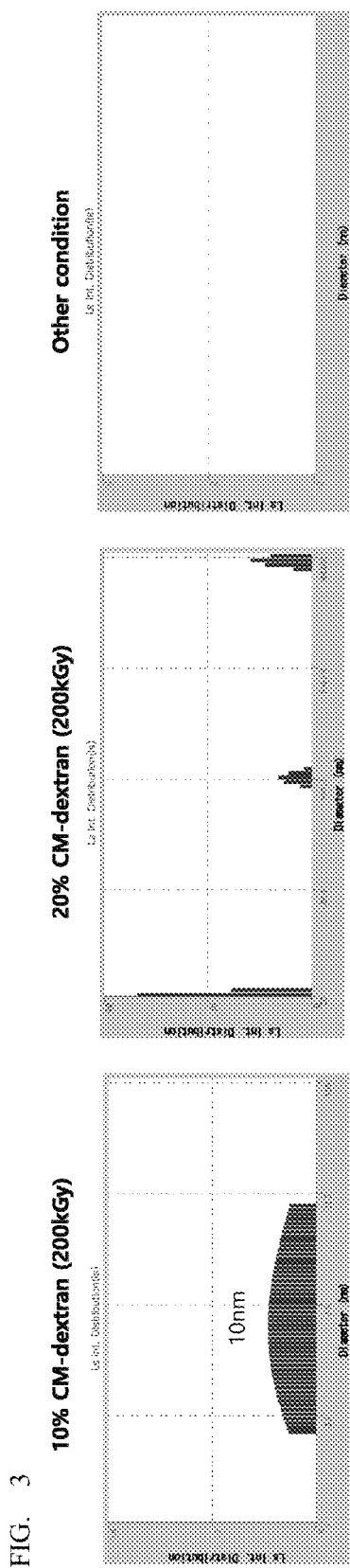
FIG. 3 illustrates the results of confirming, through DLS, the generation of nanoparticles after electron beam irradiation of carboxymethyl-dextran aqueous solutions with different concentrations.

When the electron beam with 200 kGy was applied to the 20% carboxymethyl dextran solution, several peaks were observed in the DLS measurement, and the measurement was not favorably carried out under other conditions, and thus it was confirmed that nanoparticles were not favorably formed (FIG. 3).

2-3. Preparation of Nanoparticles Derived from Polysaccharides or Oligosaccharides by Electron Beam Irradiation In addition to the carboxymethyl-dextran nanoparticles, nanoparticles were manufactured by using other polysaccharides or oligosaccharides.

Experiments were conducted by the same method as in Example 2-1 except that various polysaccharides or oligosaccharides, instead of carboxymethyl-dextran, were dissolved in water, followed by electron beam irradiation, to investigate whether nanoparticles were formed.

(1) Results of Hyaluronic Acid (10 kDa)

Experiments were conducted by irradiating 1%, 5%, and 10% (w/v %) hyaluronic acid solutions with an electron beam of 10 kGy, 50 kGy, 200 kGy.

Figure 4:
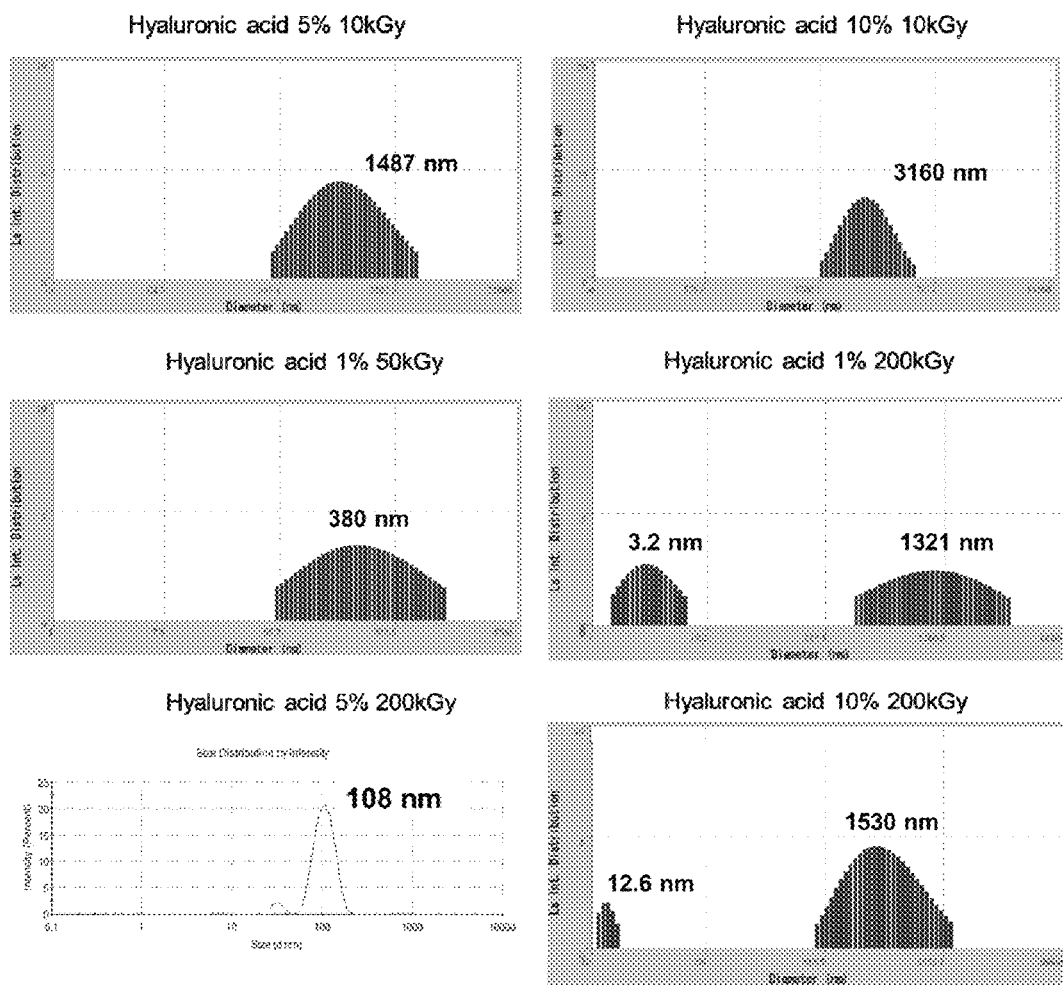
FIG. 4 illustrates the results of confirming, through DLS, the generation of nanoparticles when a hyaluronic acid aqueous solution was irradiated with an electron beam under various conditions.

As a result, it can be seen from FIG. 4 that nanogels were formed with a particle size of 108 nm under conditions of 1% and 50 kGy and a particle size of 380 nm under 5% and 200 kGy. It can be confirmed that under the other conditions, very large-sized particles were generated or several peaks were observed, and thus nanogels with a uniform particle size were not formed.

(2) Results of Mannan (0.7 kDa)

Experiments were conducted by irradiating 1%, 5%, and 10% (w/v %) mannan solutions with an electron beam of 10 kGy, 50 kGy, 200 kGy.

Figure 5:
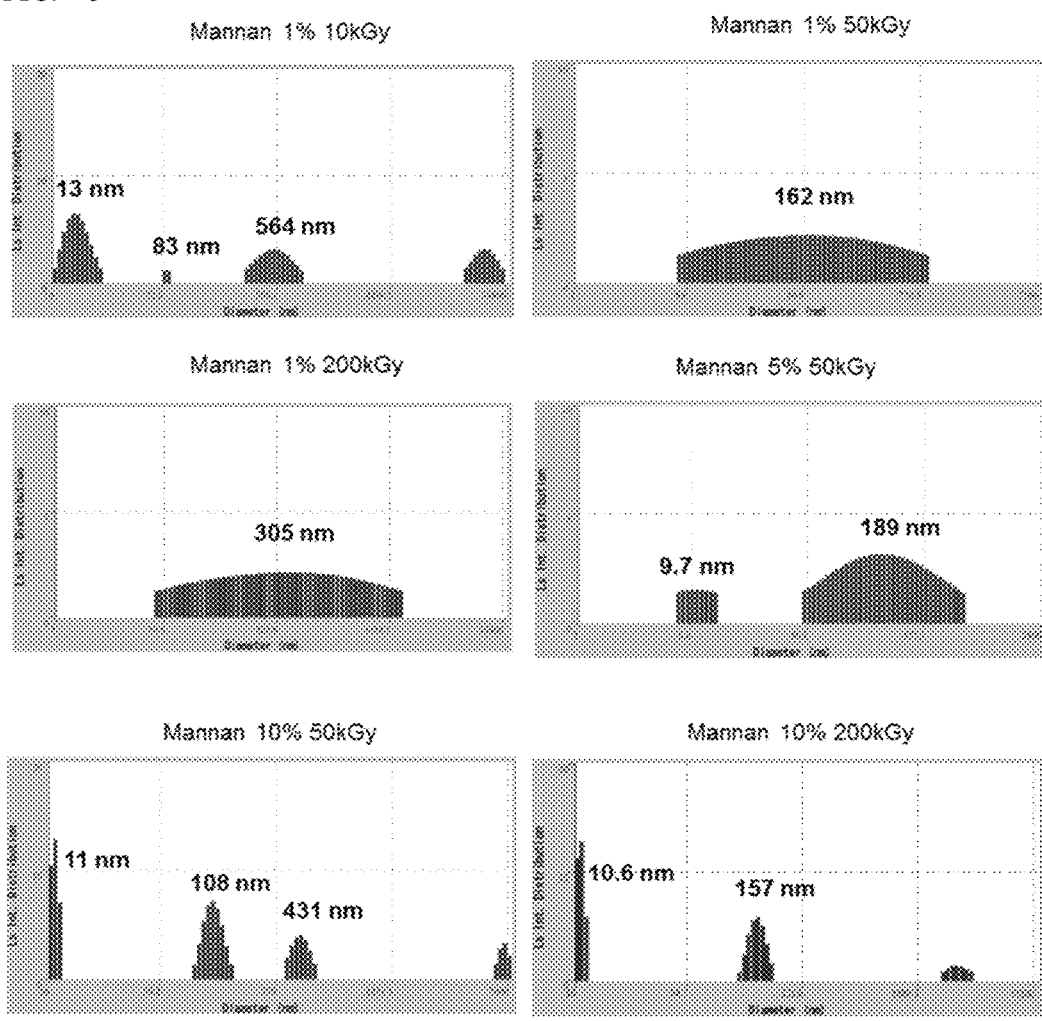
FIG. 5 illustrates the results of confirming, through DLS, the generation of nanoparticles when a mannan aqueous solution was irradiated with an electron beam under various conditions.

As a result, it can be seen from FIG. 5 that nanogels were formed with a particle size of 162 nm under conditions of 1% and 50 kGy and a particle size of 305 nm under 5% and 200 kGy. It can be confirmed that under the other conditions, very large-sized particles were generated or several peaks were observed, and thus nanogels with a uniform particle size were not formed.

(3) Results of β-Cyclodextrin (1.1 kDa)

Experiments were conducted by irradiating 0.1%, 1%, and 5% (w/v %) β-cyclodextrin solutions with an electron beam of 10 kGy, 50 kGy, 200 kGy.

Figure 6:
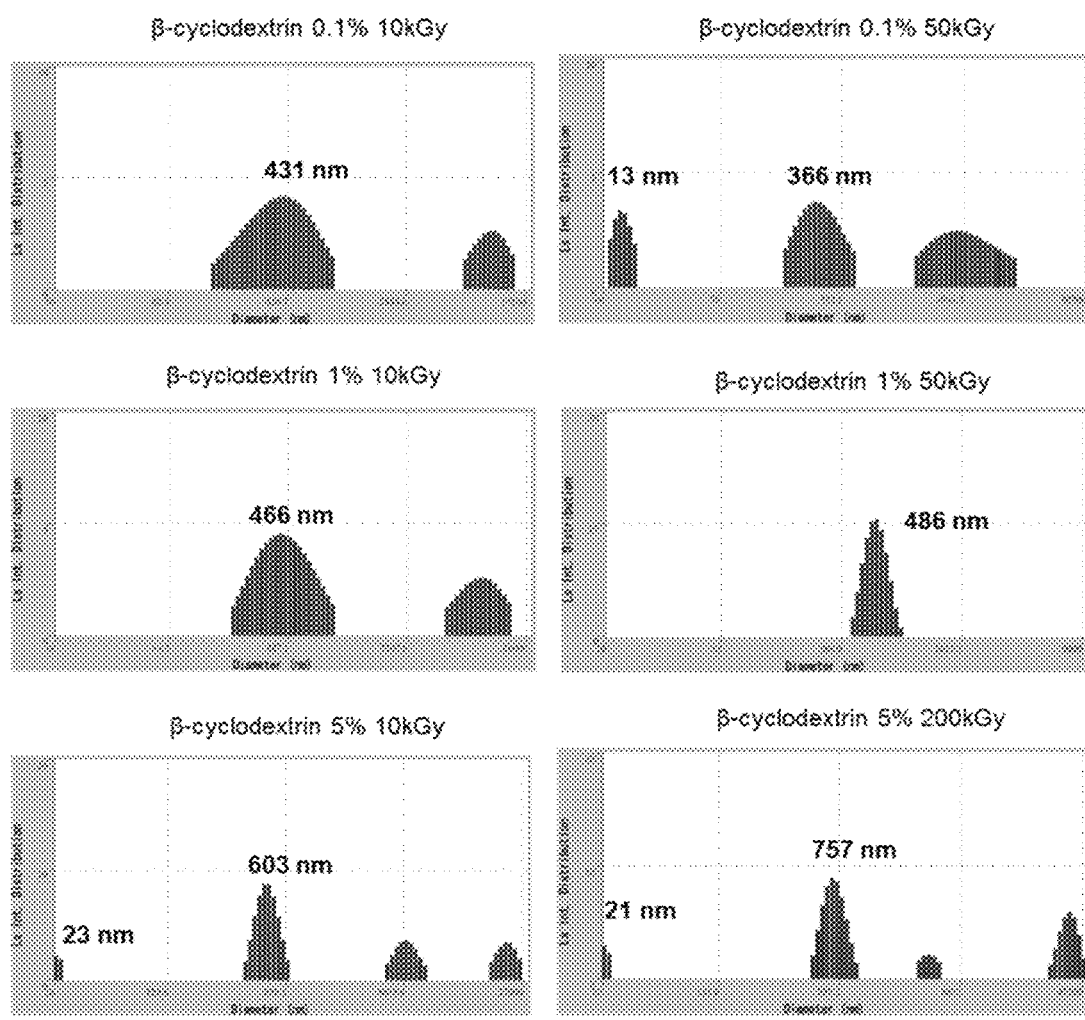
FIG. 6 illustrates the results of confirming, through DLS, the generation of nanoparticles when a β-cyclodextrin aqueous solution was irradiated with an electron beam under various conditions.

As a result, it can be seen from FIG. 6 that nanogels were formed with a particle size of 486 nm under conditions of 1% and 50 kGy. It can be confirmed that under the other conditions, several peaks were observed, and thus nanogels with a uniform particle size were not formed.

(4) Results of Alginate (33 kDa)

Experiments were conducted by irradiating 1%, 5%, and 10% (w/v %) alginate solutions with an electron beam of 10 kGy, 50 kGy, 200 kGy.

Figure 7:
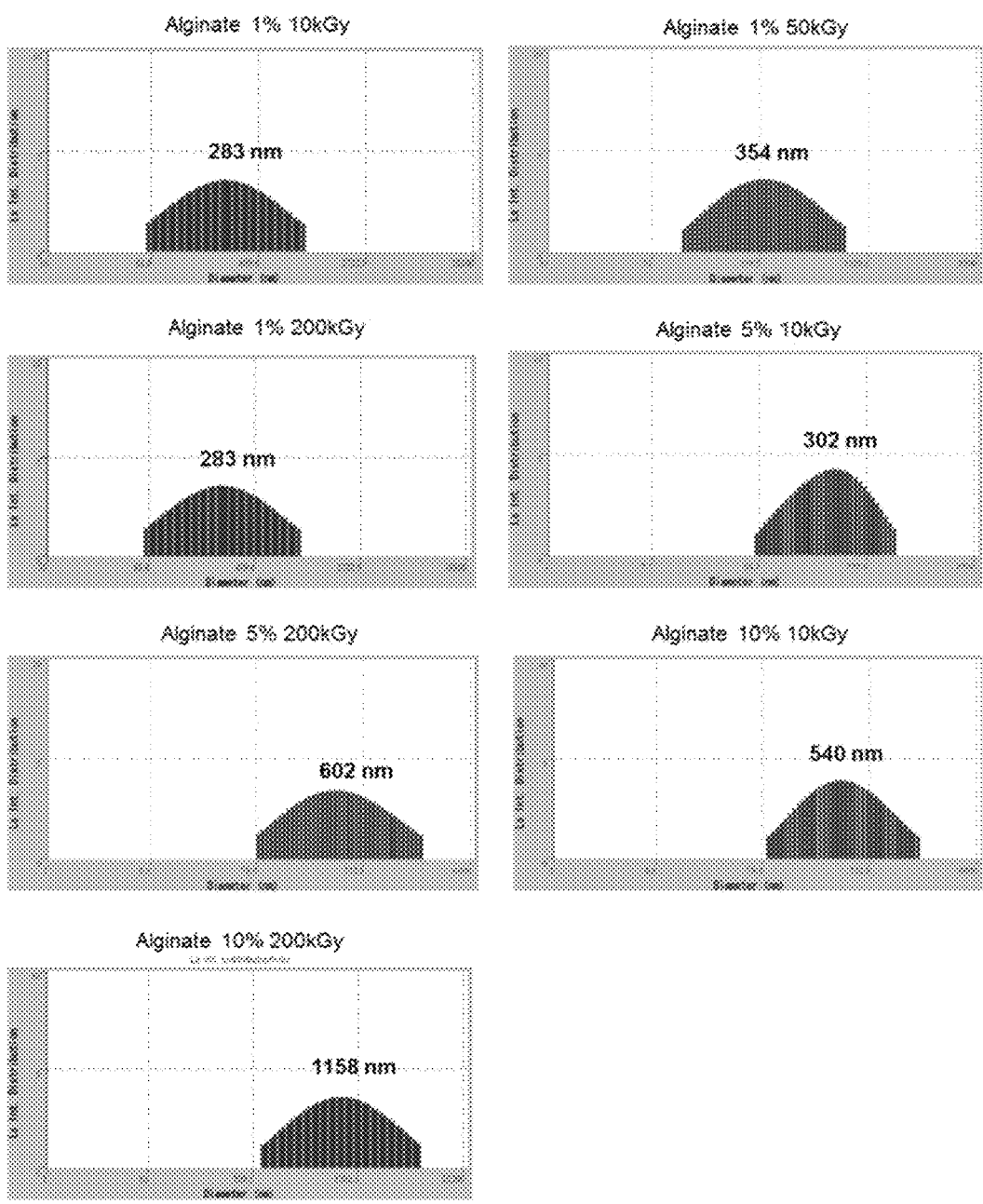
FIG. 7 illustrates the results of confirming, through DLS, the generation of nanoparticles when an alginate aqueous solution was irradiated with an electron beam under various conditions.

As a result, it can be seen from FIG. 7 that nanogels were formed with a particle size of 283 nm under conditions of 1% and 10 kGy, a particle size of 354 nm under conditions of 1% and 50 kGy, a particle size of 283 nm under conditions of 5% & 1% and 200 kGy, a particle size of 302 nm under conditions of 5% and 10 kGy, a particle size of 602 nm under conditions of 5% and 200 kGy, and a particle size of 540 nm under conditions of 10% and 10 kGy.

(5) Results of Fructo-Oligosaccharide

Experiments were conducted by irradiating 1%, 5%, 10%, 20%, 30%, and 40% (w/v %) fructo-oligosaccharide solutions with an electron beam of 10 kGy, 50 kGy, 200 kGy.

Figure 8:
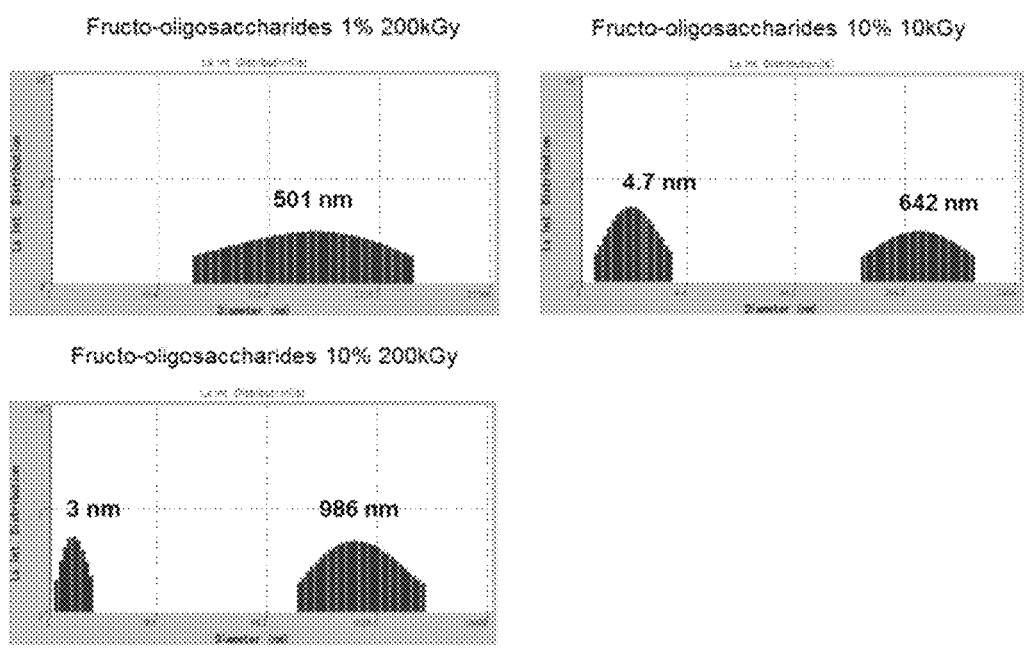
FIG. 8 illustrates the results of confirming, through DLS, the generation of nanoparticles when a fructo-oligosaccharide aqueous solution was irradiated with an electron beam under various conditions.

As a result, it can be seen from FIG. 8 that nanogels were formed with a particle size of 501 nm under conditions of 1% and 200 kGy. Meanwhile, it can be confirmed that also under conditions of 10% and 10 kGy and 10% and 200 kGy, nanoparticles were formed although the particle size is not uniform. Under the other conditions, the particle size was very large or several peaks were observed, and thus nanoparticles were not normally formed.

(6) Results of Isomalto-Oligosaccharide

Experiments were conducted by irradiating 1%, 5%, 10%, 20%, 30%, and 40% (w/v %) isomalto-oligosaccharide solutions with an electron beam of 10 kGy, 50 kGy, 200 kGy.

Figure 9:
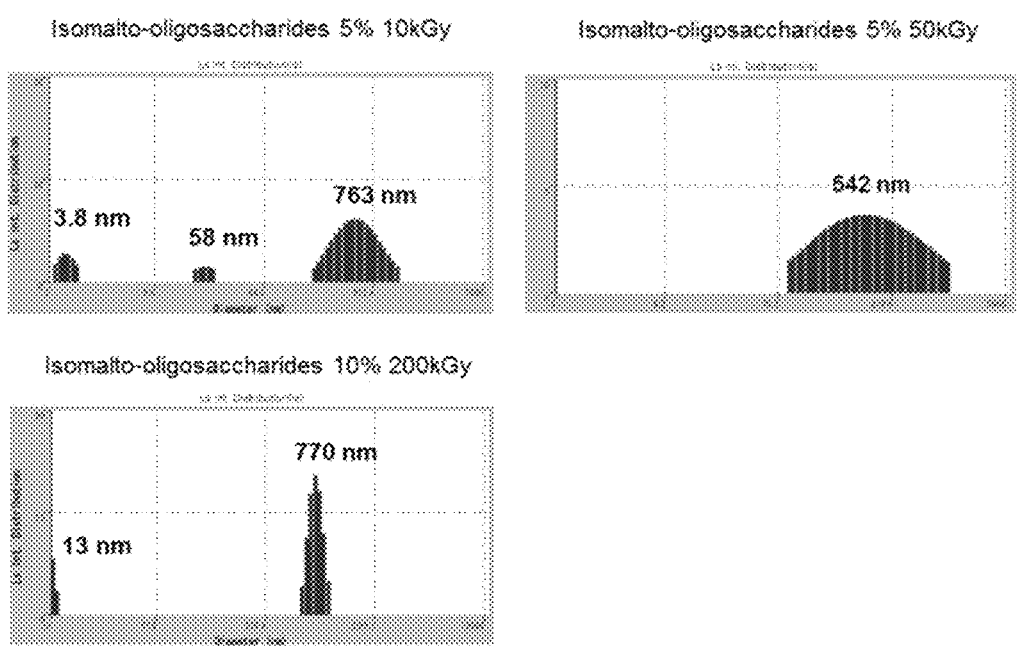
FIG. 9 illustrates the results of confirming, through DLS, the generation of nanoparticles when an isomalto-oligosaccharide aqueous solution was irradiated with an electron beam under various conditions.

As a result, it can be seen from FIG. 9 that nanogels were formed with a particle size of 542 nm under conditions of 5% and 50 kGy. Meanwhile, it can be confirmed that also under conditions of 5% and 10 kGy and 10% and 200 kGy, nanoparticles were formed although the particle size is not uniform. Under the other conditions, the particle size was very large or several peaks were observed, and thus nanoparticles were not normally formed.

(7) Results of Fucoidan

Experiments were conducted by irradiating 0.5%, 1%, and 5% (w/v %) fucoidan solutions with an electron beam of 10 kGy, 50 kGy, 200 kGy.

Figure 10:
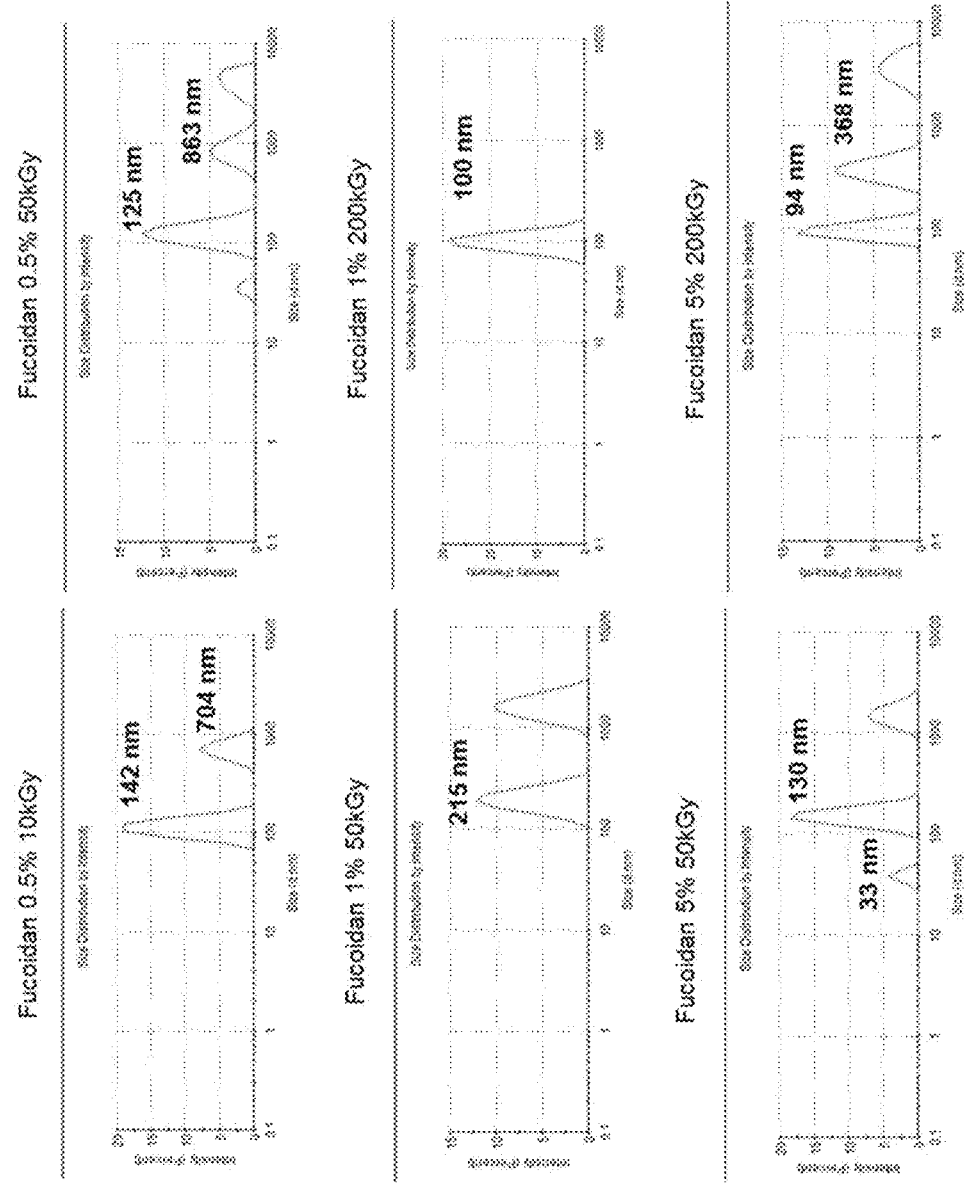
FIG. 10 illustrates the results of confirming, through DLS, the generation of nanoparticles when a fucoidan aqueous solution was irradiated with an electron beam under various conditions.

As a result, it can be seen from FIG. 10 that nanogels were formed with a particle size of 100 nm under conditions of 1% and 200 kGy. It can be confirmed that under the other conditions, several peaks were observed, and thus nanogels with a uniform particle size were not formed.

(8) Results of Chitosan (5 kDa)

Experiments were conducted by irradiating 0.5%, 1%, and 5% (w/v %) chitosan solutions with an electron beam of 10 kGy, 50 kGy, 200 kGy.

Figure 11:
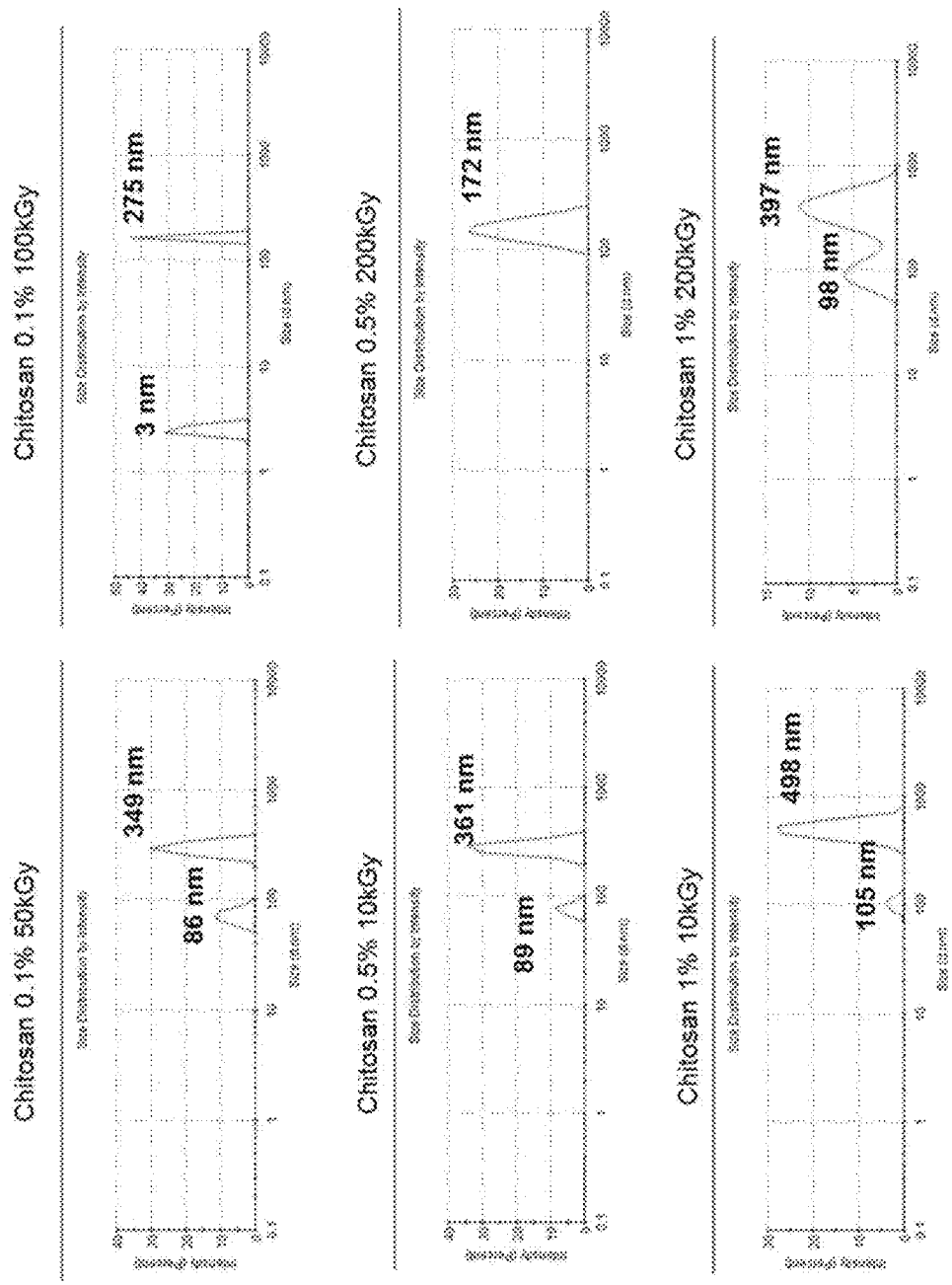
FIG. 11 illustrates the results of confirming, through DLS, the generation of nanoparticles when a chitosan aqueous solution was irradiated with an electron beam under various conditions.

As a result, it can be seen from FIG. 11 that nanogels were formed with a particle size of 172 nm under conditions of 0.5% and 200 kGy. Meanwhile, it can be confirmed that also under conditions of 0.1% and 50 kGy, 0.1% and 100 kGy, 0.5% and 10 kGy, 1% and 10 kGy, and 1% and 200 kGy, nanoparticles were formed although the particle size was not uniform. Under the other conditions, the particle size was very large or several peaks were observed, and thus nanoparticles were not normally formed.

Example 3

Evaluation of Physical Properties of Carboxymethyl-Dextran Nanoparticles (CM-DNP)—Characteristics of Gel The samples irradiated with the electron beam were dialyzed using a dialysis membrane tube with a size of 3.5-6 kDa while water containing NaCl was exchanged two times a day for 5 days. It was investigated through DLS whether the particle size was changed, but it could be confirmed that the particle size did not change during the dialysis procedure. Thereafter, the samples were freeze-dried to calculate the yield of nanoparticles formed through crosslinking by the irradiated electron beam. A yield of about 43% was obtained and a total of 8.2 g of nanoparticles were obtained.

Figure 12:
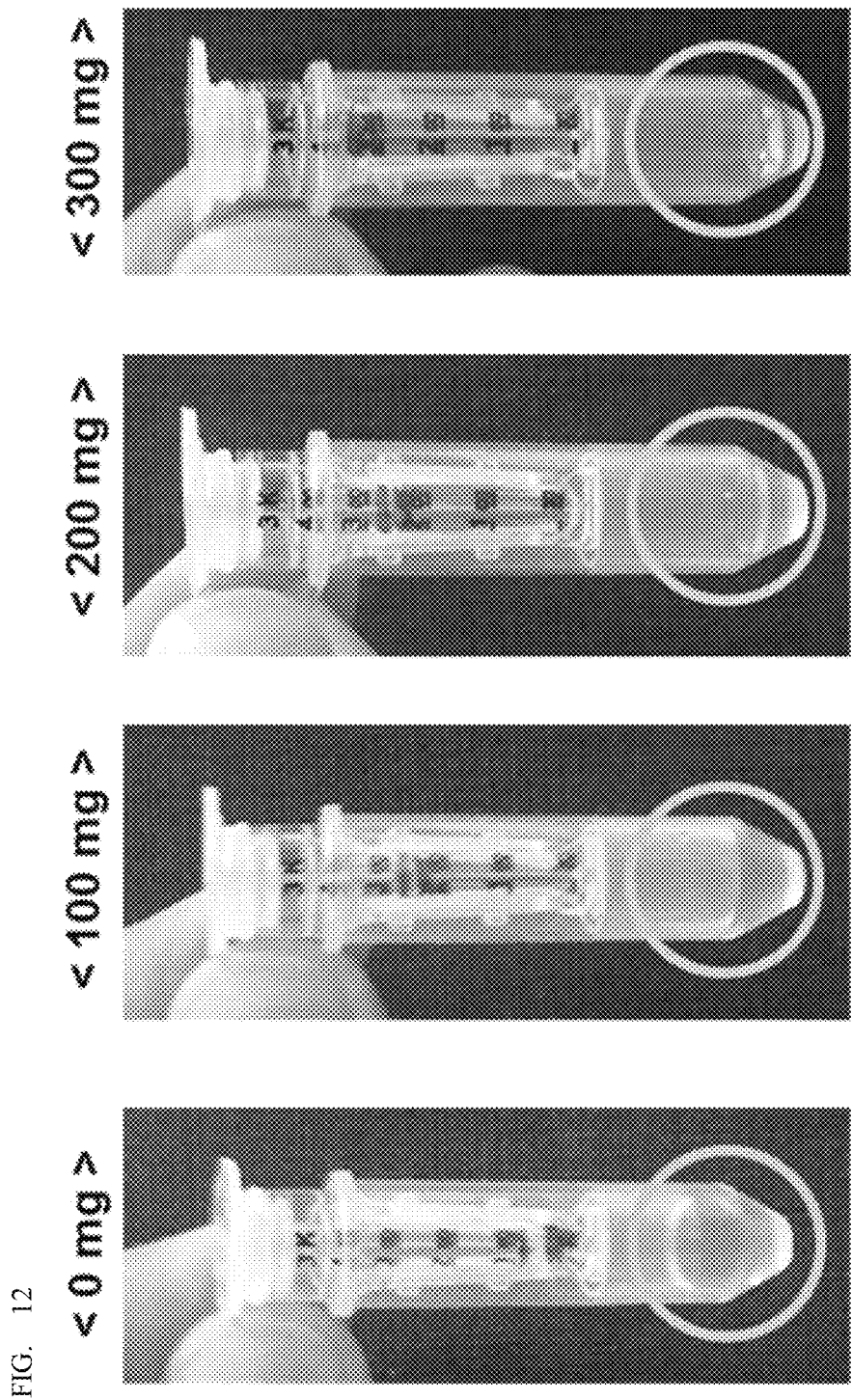
FIG. 12 shows views of confirming hydrogel characteristics by comparing differences in amount of water remaining on tube bottoms after centrifugation, according to the concentration of carboxymethyl-dextran nanoparticles.

Experiments were conducted, by using nanoparticles manufactured according to the examples above, to investigate whether these nanoparticles show gel characteristics. After 0 mg, 100 mg, 200 mg, and 300 mg of CM-DNP were dissolved in 400 uL of water, centrifugation using a centrifugal filter (YM-3) with a 3 kDa membrane was repeatedly conducted three times at 13000 rpm for 30 min. It was investigated how the degree of water swelling varies according to the concentration of CM-DNP. As a result, it could be confirmed that the amount of water falling to the bottom of the tube after centrifugation was different depending on the concentration of CM-DNP, and the higher the concentration of CM-DNP, the lower the amount of water. It can be confirmed from these results that the synthesized CM-DNP nanoparticles had gel characteristics (FIG. 12).

Example 4

Figure 13:
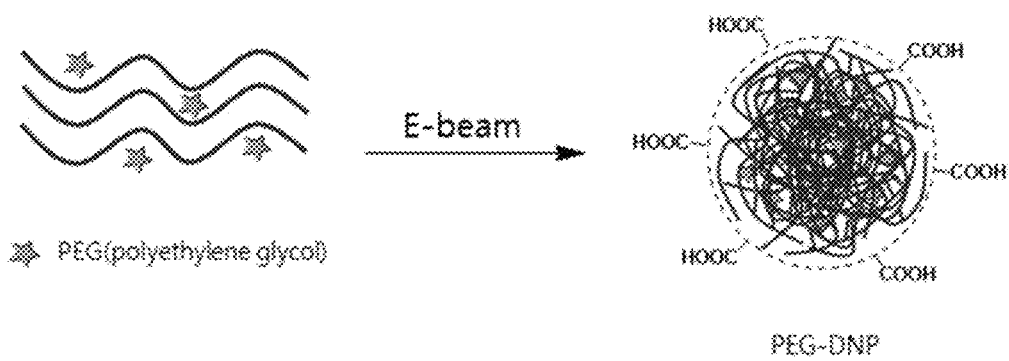
FIG. 13 is a schematic diagram showing a manufacture procedure of a polyethylene glycol and carboxymethyl-dextran mixed nanoparticle using an electron beam.

Synthesis of Carboxymethyl-Dextran Nanoparticles (CM-DNP) Mixed with Polyethylene Glycol (PEG) Through Electron Beam Irradiation It was planned to study the effect of organic molecules, which have already been used in clinical trials, on the formation of dextran nanoparticles and physical properties thereof by adding the organic molecules, in addition to dextran, while polyethylene glycol (PEG) already widely used in clinical trials was used as the organic molecules to be added (FIG. 13).

Figure 14:
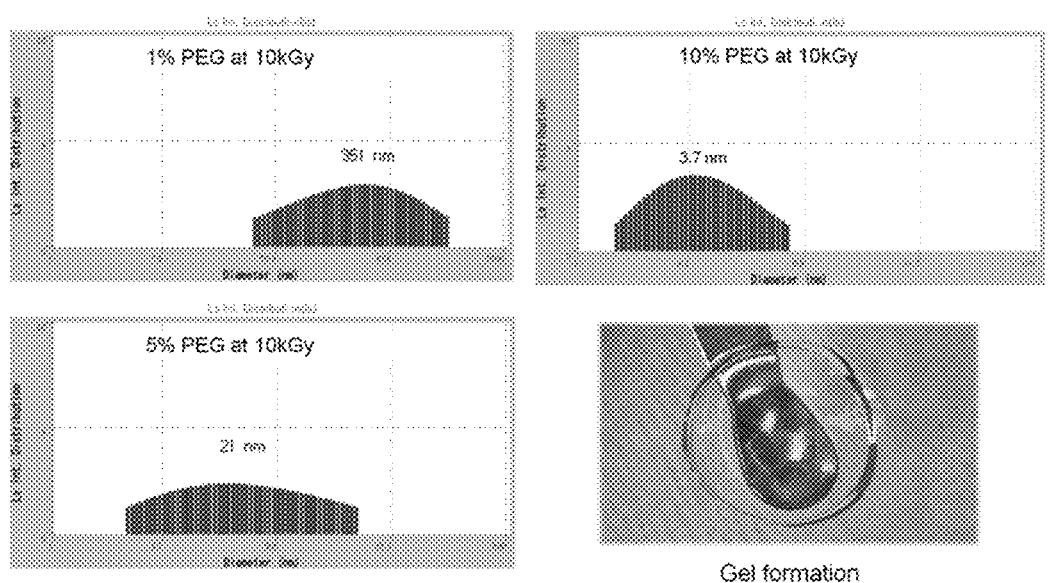
FIG. 14 illustrates diagrams of confirming the formation of PEG nanoparticles and the particle size thereof when electron beams with various energy intensities were irradiated.

4-1. Generation of Polyethylene Glycol (PEG) Nanoparticles by Electron Beam Irradiation First, experiments for investigating whether PEG itself induces crosslinking at the time of electron beam irradiation were conducted, and experiments was conducted by electron beam irradiation at several energy intensities with varying PEG concentrations. In the experiments, PEG of 6 kDa was used. The PEG was dissolved in water to prepare solutions with concentrations of 1%, 5%, and 10% (w/v), and the electron beam was applied with energy intensities of 10 kGy, 30 kGy, 50 kGy, 100 kGy, and 200 kGy. When the energy intensity increased to 30 kGy or higher, the colors of the samples became turbid and the tendency of bulk gel formation was confirmed. When the concentration of PEG was low, the tendency that a larger sized nanogel was produced was confirmed (FIG. 14).

4-2. Preparation of Nanoparticles of PEG and Carboxymethyl-Dextran Mixture by Electron Beam Irradiation It could be directly confirmed that crosslinking occurred when the PEG solution was irradiated with the electron beam. Experiments were conducted to investigate whether crosslinking was favorably done when a mixture of PEG and carboxymethyl dextran was irradiated with an electron beam and whether nanoparticles having different sizes and physical properties from the nanoparticles manufactured using only carboxymethyl dextran were manufactured.

It was investigated whether nanoparticles were formed, by preparing dextran and PEG with different concentrations of each other, followed by electron beam irradiation with 10 kGy, 50 kGy, and 200 kGy, and then measuring the size of the samples using DLS.

Figure 15:
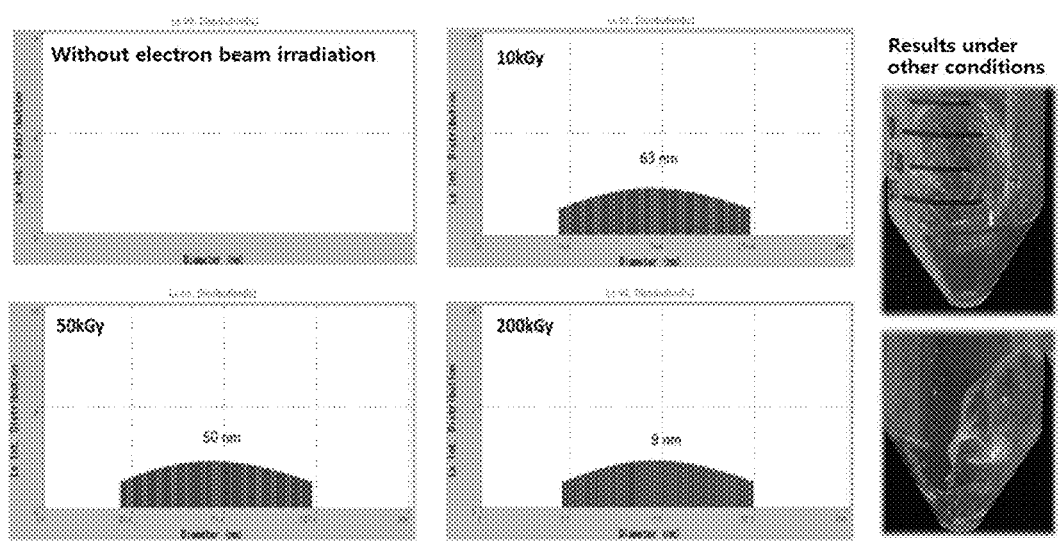
FIG. 15 shows DLS results of nanoparticles formed by irradiating a mixed aqueous solution of 10% carboxymethyl-dextran and 1% polyethylene glycol with an electron beam.

The formation of nanogels were confirmed in the electron beam irradiation using 10% carboxymethyl dextran and 1% PEG unlike the other conditions. Bulky gels were formed under the other conditions (results not shown). The results of measuring the size of samples by DLS were 63 nm at 10 kGy, 50 nm at 50 kGy, and 9 nm at 200 kGy, and thus it could be confirmed that the size of nanoparticles showed a tendency to decrease as the irradiated energy increases (FIG. 15).

4-3. Yield of PEG and Carboxymethyl-Dextran Mixed Nanoparticles (PEG-DNP)

As described above, the nanoparticles were well formed even when the mixture of 1% PEG and 10% carboxymethyl-dextran were irradiated with an electron beam at energy densities of 10, 50, and 200 kGy. Then, in order to investigate the yield of formation of nanoparticles, the samples were dialyzed using a dialysis membrane tube with a size of 3.5-5 kDa while water containing NaCl was exchanged two times a day for days, and then the respective samples were freeze-dried to calculate the yield of nanoparticles manufactured through crosslinking by electron beam irradiation, and as a result, all the samples under the respective energy conditions showed a yield of 24-36%.

Experiments were conducted wherein a much larger amount of PEG-carboxymethyl-dextran nanoparticles (PEG-DNP) were synthesized at the 200 kGy electron beam irradiation condition under which the nanoparticles with a size of 9-10 nm were generated. As a result, a size of about 10 nm was reproducibly shown, and since the experiments were massively conducted, the amount lost in each step was reduced, leading to a yield of about 52%, higher than before, and a total of 2 g of nanoparticles.

4-4. Analysis of PEG-DNP Structure

In order to investigate whether the production of PEG and CM-DNP mixed nanoparticles by electron beam irradiation results from the formation of nanoparticles by crosslinking of only PEG through electron beam irradiation (that is, in order to investigate whether the produced nanoparticles were formed by inter-molecular crosslinking of PEG and carboxymethyl-dextran), experiments to investigate whether both PEG and dextran were present in the produced nanoparticles and whether peaks of PEG or dextran could be confirmed were conducted by performing NMR analysis of CM-DNP obtained in example 4-3 above.

Figure 16:
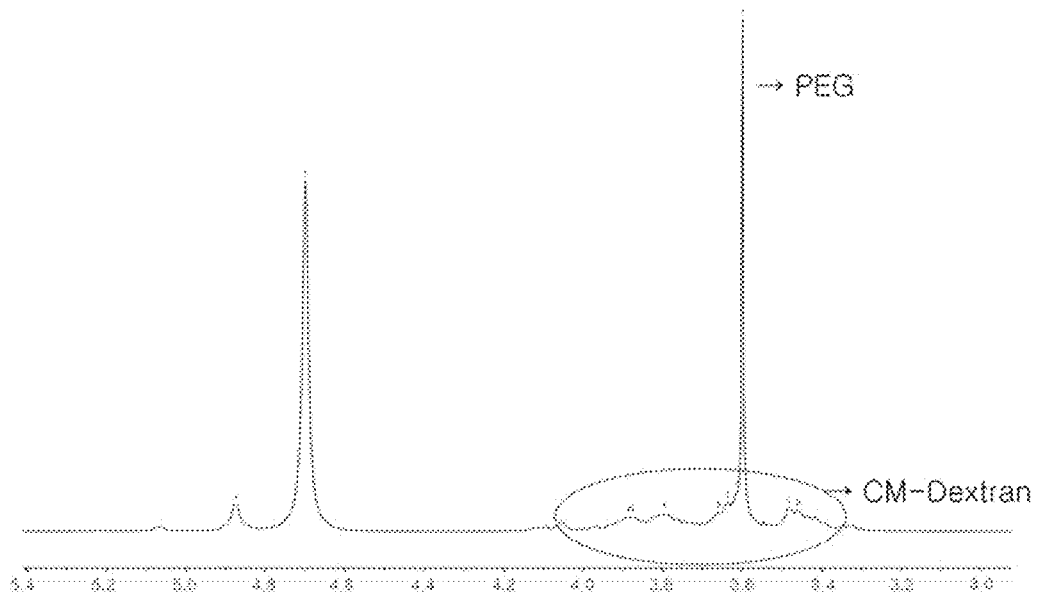
FIG. 16 is a diagram showing $^1$H-NMR results of polyethylene glycol and carboxymethyl-dextran mixed nanoparticles.

In order to perform analysis using $^1$H-NMR, the samples were dissolved in $D_2O$ and analyzed. As a result, the peaks of dextran together with the peaks of PEG could be observed, indicating that the produced nanoparticles were obtained by crosslinking of PEG and dextran together (FIG. 16).

Figure 17:
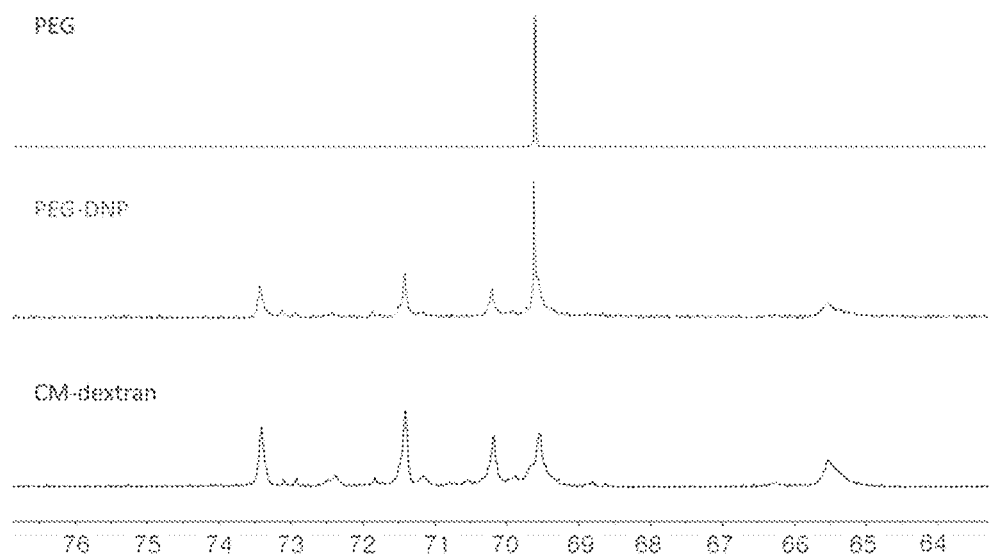
FIG. 17 is a diagram showing $^{13}$C-NMR results of polyethylene glycol and carboxymethyl-dextran mixed nanoparticles.

The results of $^{13}$C-NMR analysis also confirmed the peaks of dextran together with the peaks of PEG, again indicating that the produced nanoparticles were obtained by crosslinking of PEG and dextran together (FIG. 17).

Example 5

Chelate Conjugation of Carboxymethyl-Dextran Nanoparticle and Cu-64 Radioactive Labeling Experiments were conducted wherein various chelates were conjugated to the synthesized CM-DNP, followed by radioactive labeling with Cu-64. In order to conduct labeling experiments using Cu-64 on nanoparticles, chelates were first conjugated to the nanoparticles. Three types of chelates, DOTA-Bn-p-$NH_2$, DOTA-GA-$NH_2$, and TE2A-$NH_2$, were used.

Figure 18:
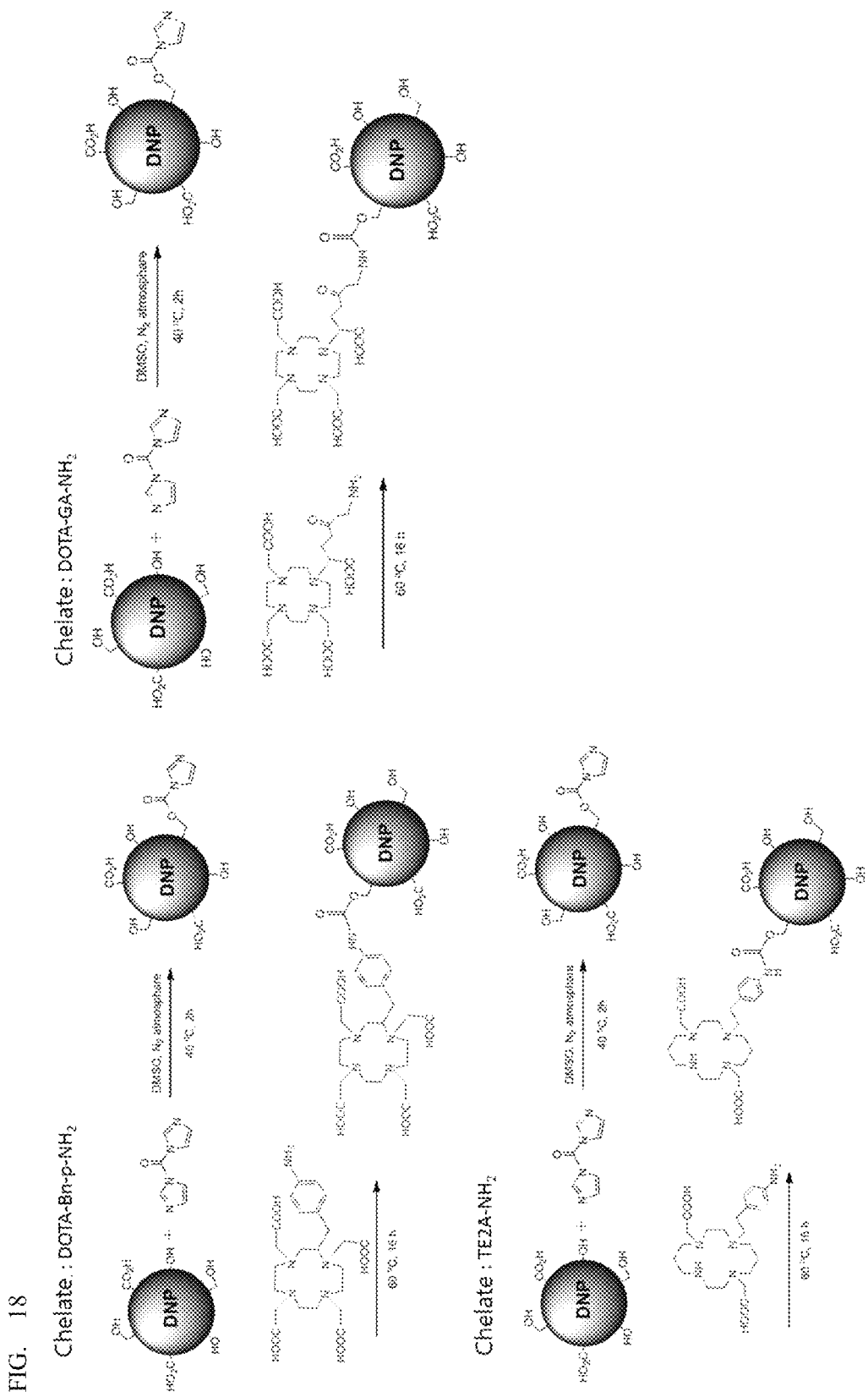
FIG. 18 is a diagram showing structures in which chelates are conjugated to carboxymethyl-dextran nanoparticles.

CM-DNP (100 mg) was placed in a round-bottomed flask, and then dissolved by addition of DMSO (5 mL), and thereafter, carbodiimidazole (CDI, 10 mg) was added, and then the reaction was conducted with stirring at 40° C. for 2 hours under nitrogen atmosphere. After the reaction, it was confirmed using TLC whether unreacted CDI remains with proper stationary phase and mobile phase conditions (C-18, $CH_2Cl_2$:MeOH=10:1). When the CDI was completely reacted, three kinds of chelates were added respectively, followed by reaction at 60° C. for 16 hours. Thereafter, dialysis was conducted for purification, and then the respective samples were freeze-dried, thereby obtaining dextran nanoparticles conjugated with chelates of approximately 35-45 mg (FIG. 18).

It was investigated whether the chelate-conjugated nanoparticles as above were favorably radio-labeled with Cu-64.

Figure 19:
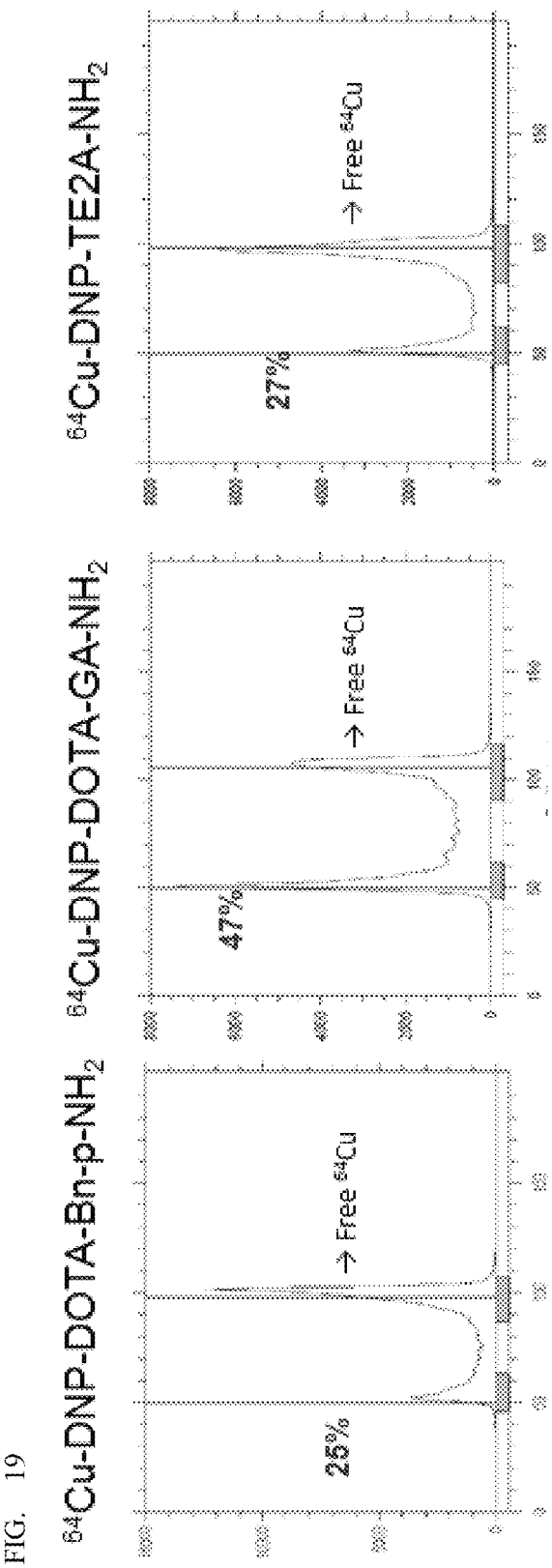
FIG. 19 is a diagram showing the Cu-64 labeling TLC results of chelate-conjugated carboxymethyl-dextran nanoparticles.

After 10 μg of carboxymethyl-dextran nanoparticles conjugated with three kinds of chelates were added to 100 μL of 0.1 M $NH_4OAc$ (pH 6.8), Cu-64 was added thereto, followed by reaction at 60° C. for 1 hour. When it was investigated, by using ITLC as a stationary phase and 50 mM EDTA as a mobile phase, whether Cu-64 labeling were favorably achieved, the labeling was confirmed to be done by 25% for DOTA-Bn-p-$NH_2$-conjugated dextran nanoparticles, 47% for DOTA-GA-$NH_2$-conjugated dextran nanoparticles, and 27% for TE2A-$NH_2$-conjugated dextran nanoparticles (FIG. 19).

Figure 20:
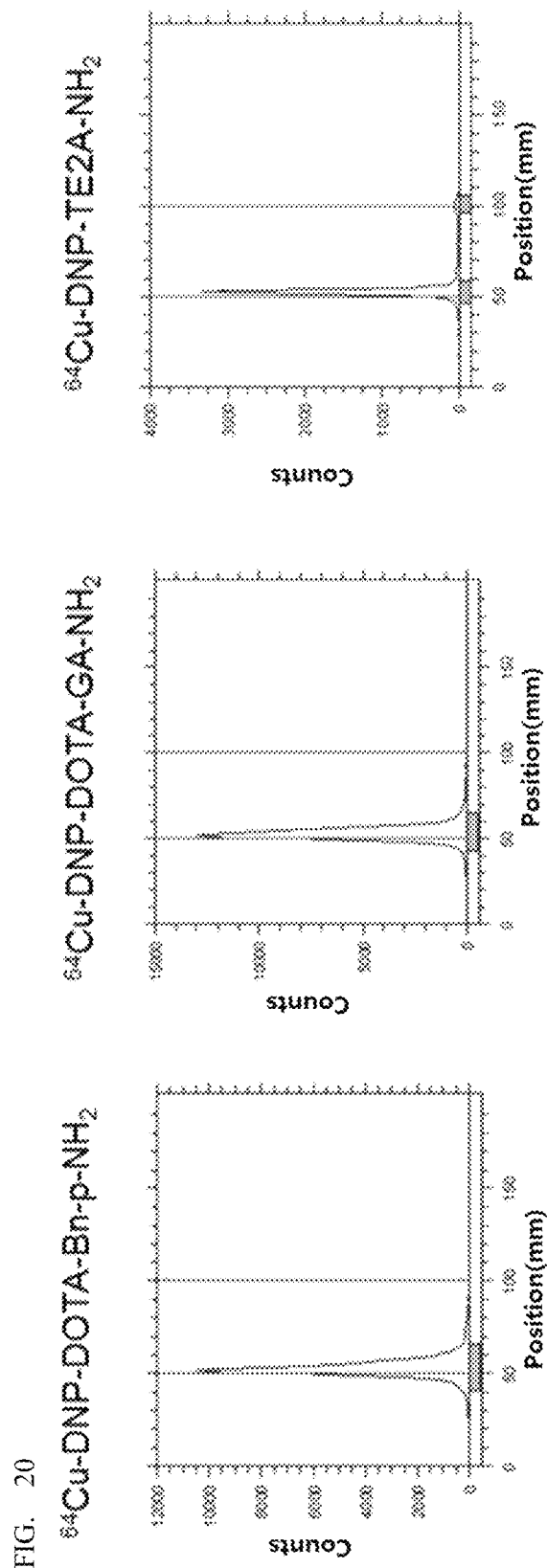
FIG. 20 is a diagram showing TLC results of Cu-64 labeled carboxymethyl-dextran nanoparticles.

Then, centrifugation was repeatedly conducted five times by using a centrifugal filter (YM-10 filter) with a 10 kDa porous membrane, and then a purification procedure of removing unlabeled free Cu-64 and separating only labeled nanoparticles was conducted, and thereafter, it was confirmed through TLC that free Cu-64 was completely removed in the separated nanoparticles (FIG. 20).

Example 6

Labeling of Carboxymethyl-Dextran Nanoparticles Using Radioactive Iodine

Figure 21:
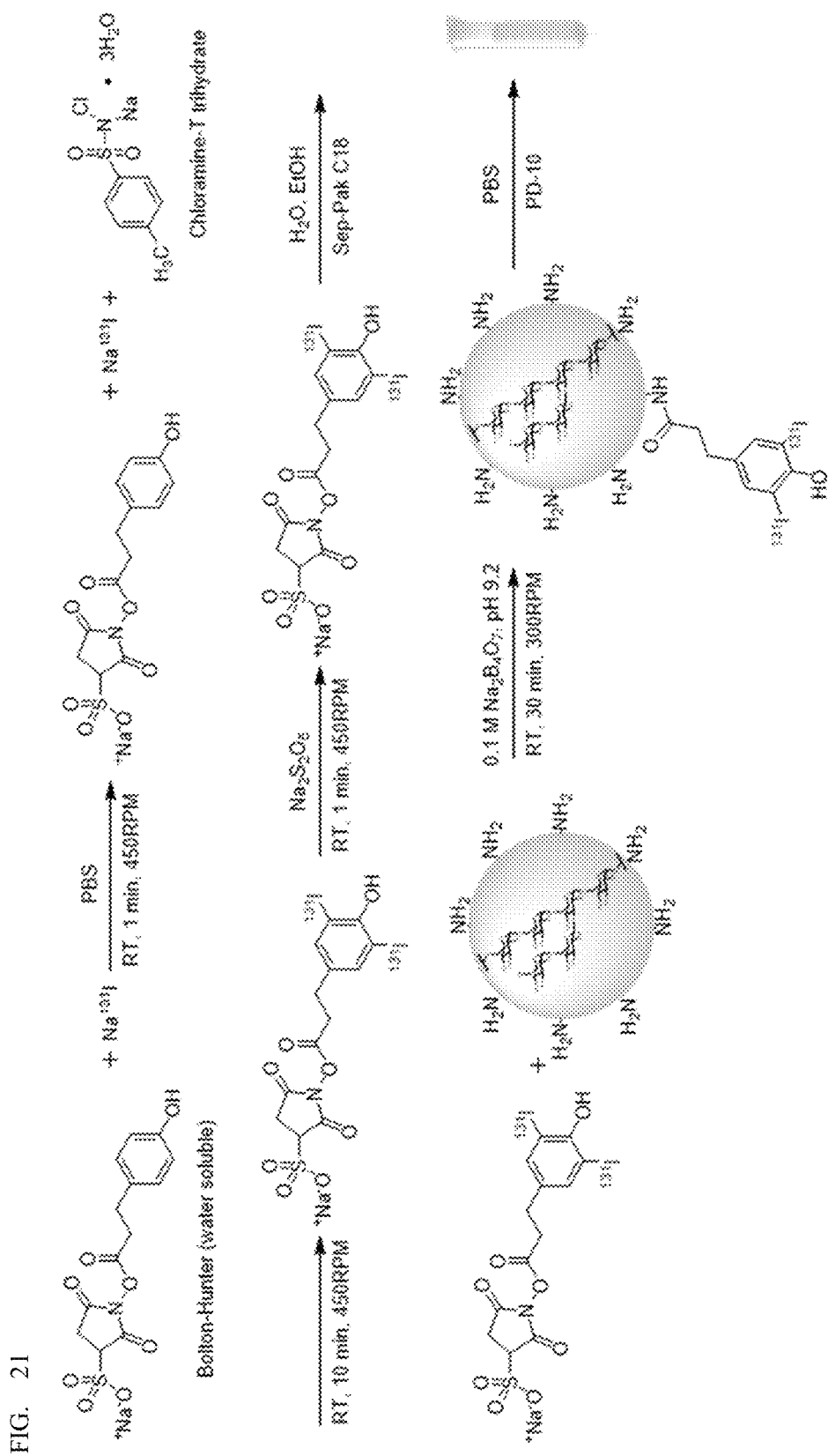
FIG. 21 is a diagram showing a radioactive iodine labeling procedure of a carboxymethyl-dextran nanoparticle using Bolton-Hunter Reagent.

The development of CM-DNP-based nuclear medicine imaging contrast agents through radionuclide labeling was conducted using radioactive iodine in addition to Cu-64. Radioiodine labeling was conducted by using a Bolton-Hunter reagent, which is a prosthetic group widely utilized. As the radioactive iodine, I-131, which has a half-life of 8 days and a relatively low price, was purchased for the experiments (FIG. 21).

Figure 22:
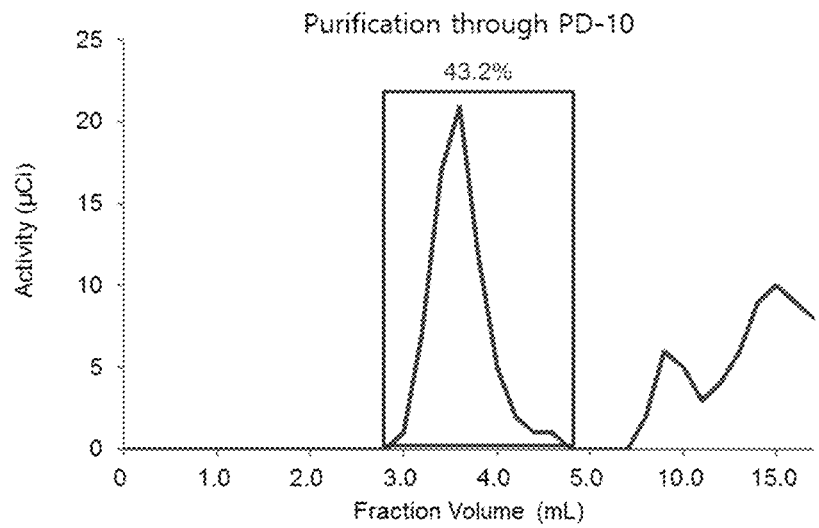
FIG. 22 is a diagram showing the Radio-TLC results of I-131 labeled carboxymethyl-dextran nanoparticles after reaction and purification.
Figure 22:
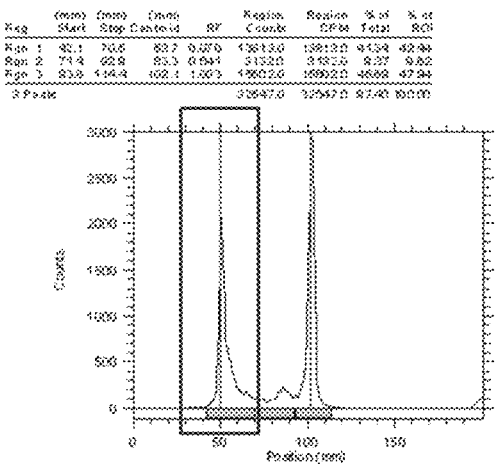
Figure 22:
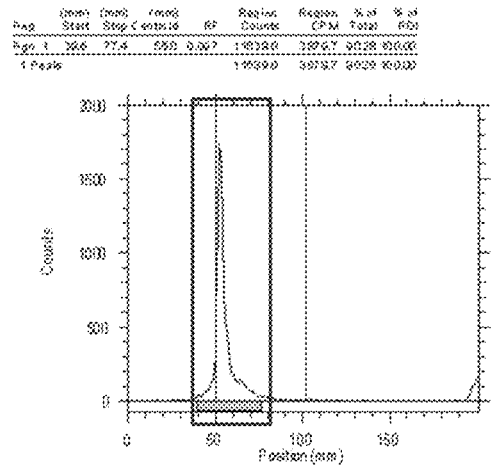

The labeling experiments were conducted using CM-DNP having a size of 10 nm. After the Bolton-Hunter reagent (1.1 µg/µL in DMSO) was reacted with I-131 and Chloramine-T (10 µg/µL in D.W) for 1 min, the reaction was stopped using sodium metabisulfite, Sep-PAK C18 was used to separate the labeled Bolton-Hunter reagent by water and ethanol. The separated Bolton-Hunter reagent and carboxymethyl-dextran nanoparticles were subjected to conjugation for 30 minutes using 0.1 M $Na_2B_4O_7$ (pH 9.2), and then the labeled nanoparticles were separated using PD-10 column (FIG. 22).

The labeling yield results after the reaction and the purification procedure using PD-10 column were investigated using radio-TLC. The labeling yield was 43%, and free I-131 was removed through the PD-10 column, thereby favorably separating only the labeled nanoparticles.

Example 7

Figure 23:
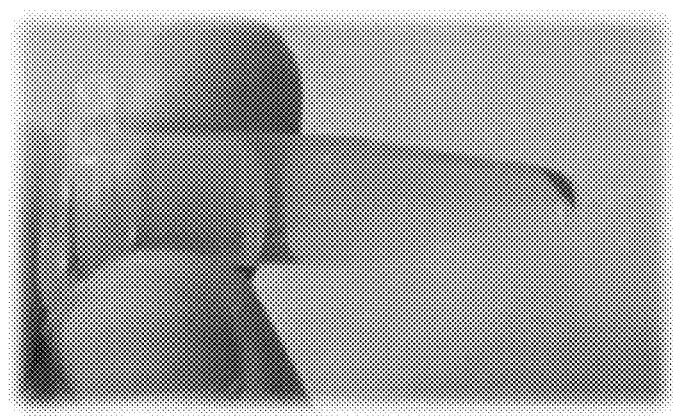
FIG. 23 shows a doxorubicin standard curve and an observation diagram of a doxorubicin-conjugated carboxymethyl-dextran nanoparticle confirmed through centrifugation.
Figure 23:
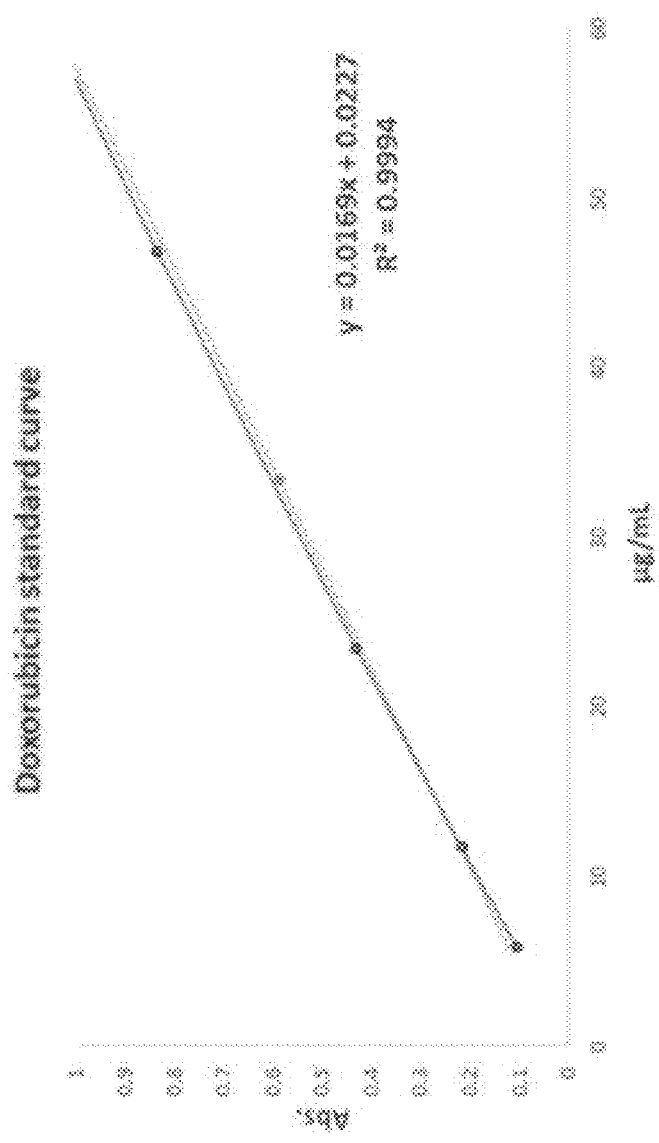

Synthesis of Doxorubicin-Conjugated Carboxymethyl-Dextran-Based Nanoparticles 7-1. Conjugation of Doxorubicin to Nanoparticles Experiments wherein doxorubicin widely used as an anticancer drug was conjugated to a dextran nanoparticle were conducted. The experiments were first conducted using CM-DNP. After 15 mg of CM-DNP with a size of 10 nm was dissolved in 3 mL of DW, the pH was adjusted to 8 using NaOH, and then a reaction was carried out by adding doxorubicin (1 mg/mL), blocking light, and stirring the mixture at room temperature overnight. After the reaction, centrifugation was carried out at 16,000 g for 90 min, so that doxorubicin-conjugated dextran nanoparticles formed pellets on the bottom. The supernatant and the pellets were separated (FIG. 23).

The amount of doxorubicin not conjugated to nanoparticles could be confirmed by measuring the absorption spectrum of the separated supernatant. The absorbance was determined at a wavelength of 481 nm, which indicates the absorption maximum for doxorubicin, and the measurement value were put into the previously prepared standard curve for doxorubicin at a wavelength of 481 nm to investigate the amount of doxorubicin remaining in the supernatant. The amount of doxorubicin used in the reaction and the amount of doxorubicin remaining in the supernatant were put into the formula below to investigate the amount of doxorubicin loaded in CM-DNP. As a result, it was confirmed that the loading efficiency (LE, %) was 78.9%.

Experiments wherein doxorubicin was also conjugated to PEG-DNP were conducted by the same method as above, and it was confirmed that LE (%) was lower, 56.1%. Therefore, experiments were conducted to find conditions that increase LE (%) of doxorubicin. When the amount of PEG-DNP used to react with 1 mg/mL of doxorubicin was reduced from 3 mg/mL to 0.5 mg/mL, it was confirmed that LE (%) increased to 72.7%. Here, it was confirmed that there was no significant difference in LE (%) even if the reaction time was reduced to 45 minutes, and thus the reaction time could be shortened.

7-2. Drug Release Rate from Doxorubicin-Conjugated Nanoparticles

Figure 24:
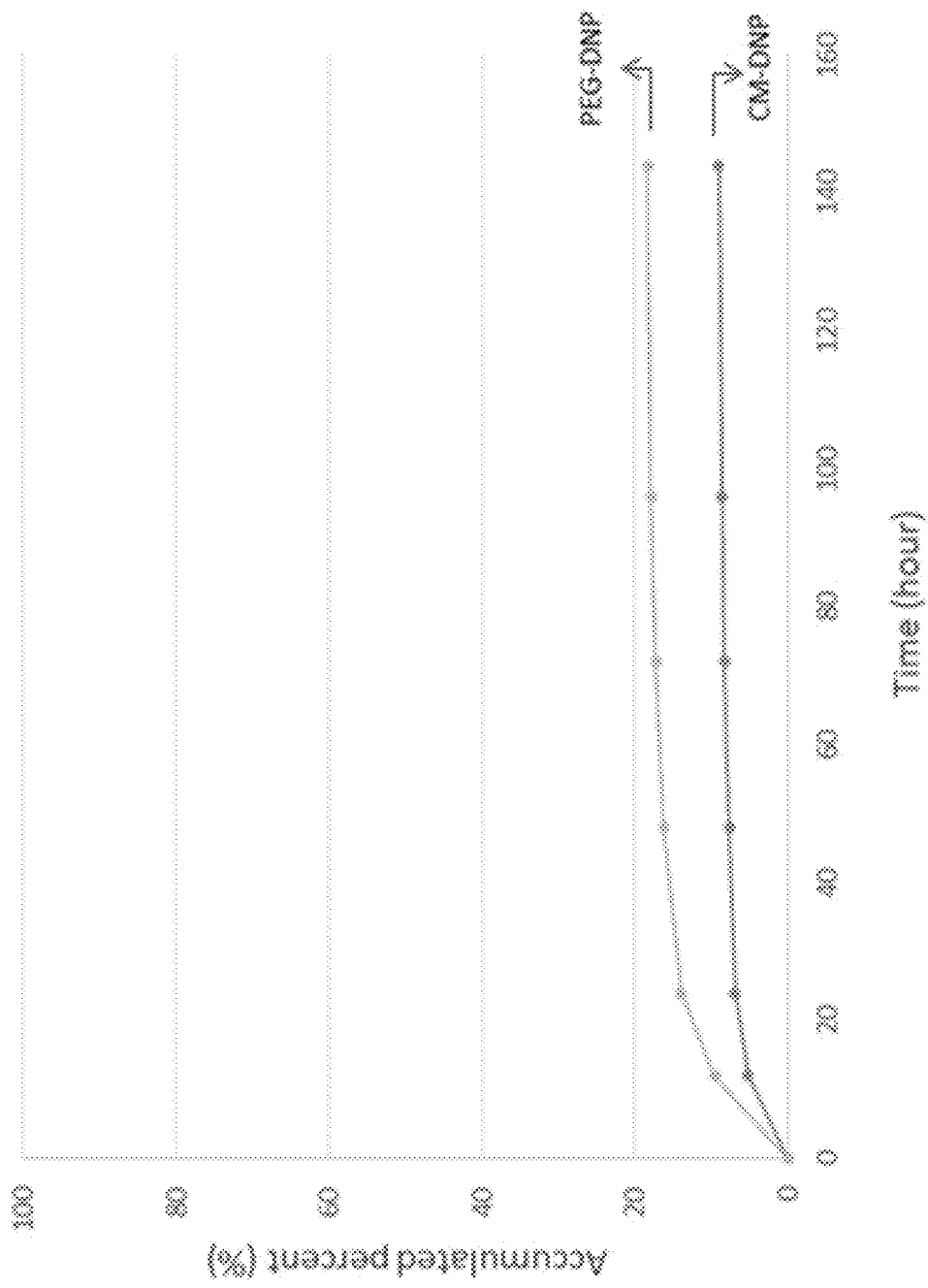
FIG. 24 shows the results of confirming the release rates of doxorubicin in a doxorubicin-conjugated carboxymethyl-dextran nanoparticle (CM-DNP) and a doxorubicin-conjugated polyethylene glycol and carboxymethyl-dextran mixed nanoparticle (PEG-DNP).
Figure 25:
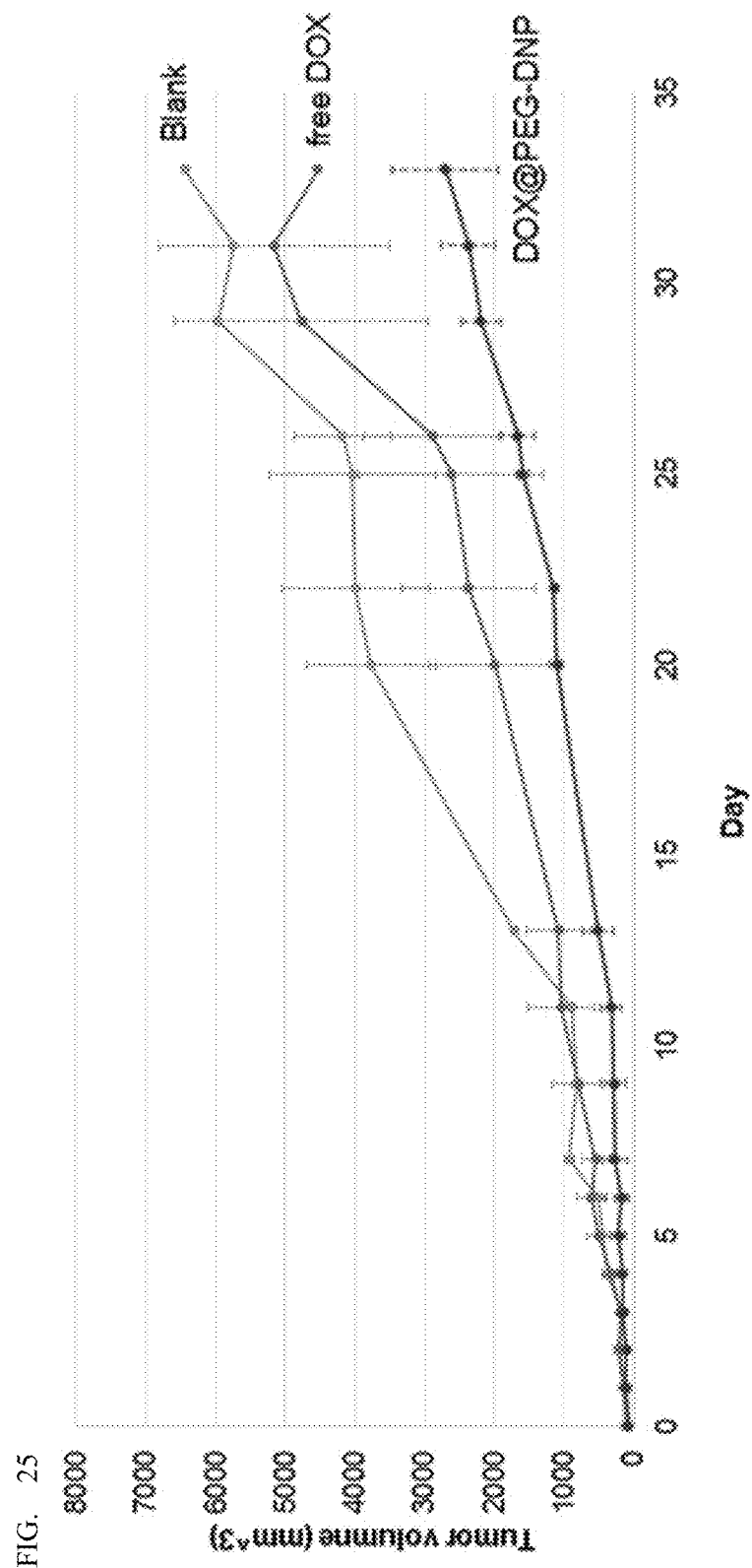
FIG. 25 shows the results of evaluating the in vivo antitumor activity of doxorubicin-conjugated nanoparticles (a blank group treated with PBS, a group treat with free doxorubicin (free DOX), and a group treated with doxorubicin-conjugated PEG-DNP (DOX @ PEG-DNP)).
Figure 26:
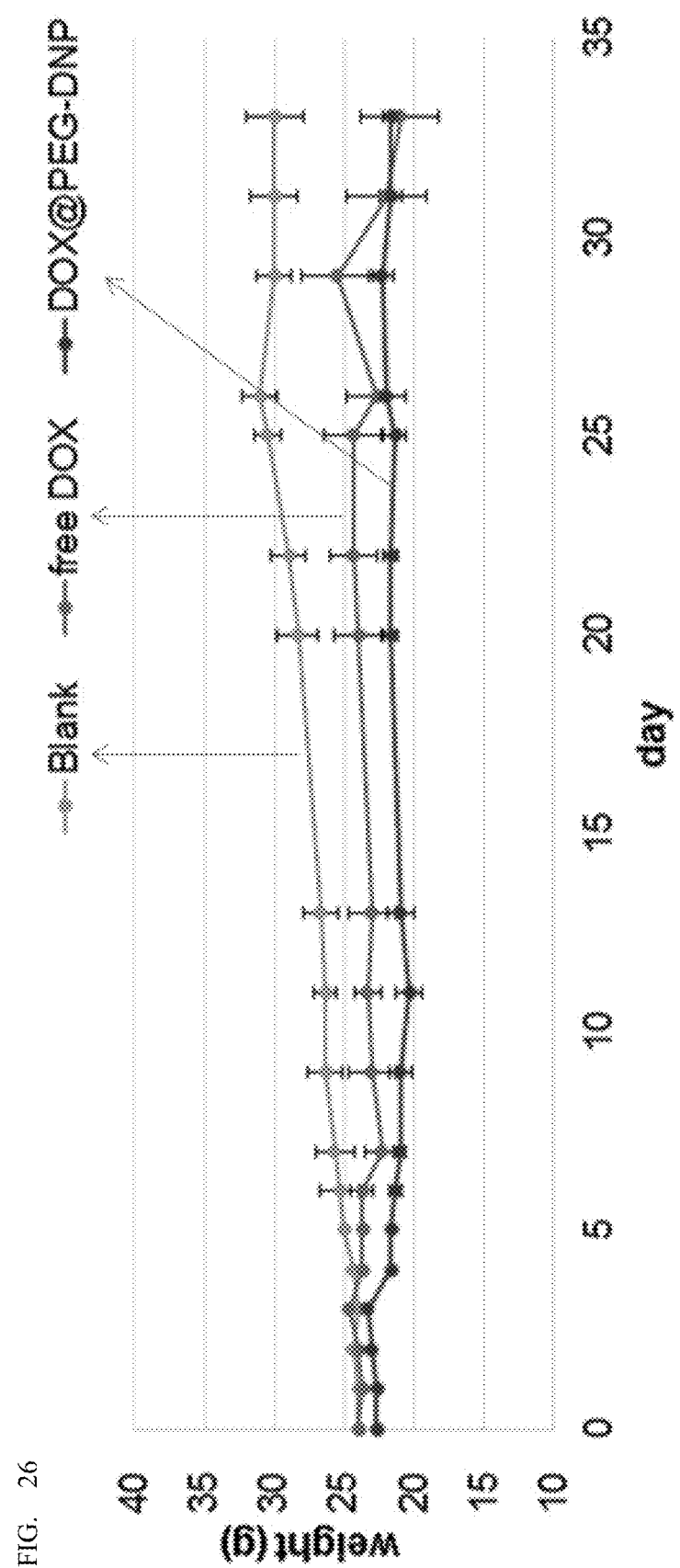
FIG. 26 is a diagram of observation of the body weight change of animals according to the administration of each drug in animal models for evaluating the in vivo antitumor activity of doxorubicin-conjugated nanoparticles (a blank group treated with PBS, a group treat with free doxorubicin (free DOX), and a group treated with doxorubicin-conjugated PEG-DNP (DOX @ PEG-DNP)).

Efflux experiments for investigating the drug release rate by using doxorubicin-conjugated carboxymethyl-dextran nanoparticles (CM-DNP) and PEG and carboxymethyl-dextran mixed nanoparticles (PEG-DNP) were conducted. In order to investigate the release rate of doxorubicin in PBS with pH 7.4 by using 10 mg of nanoparticles, samples were obtained at various time points, followed by centrifugation, and then the amount of doxorubicin present in the supernatant was investigated, and thus the amount of doxorubicin released from the nanoparticles was investigated. As a result, it was confirmed that 9.16% of doxorubicin was released out of CM-DNP over 6 days, and 18.4% of doxorubicin, which is conjugated to nanoparticles, was significantly slowly and continuously released out of PEG-DNP (FIG. 24).

7-3. Tumor Growth Inhibitory Effect of Doxorubicin-Conjugated PEG-DNP

Experiments were conducted to compare and investigate the ability of doxorubicin-conjugated dextran-based nanoparticles whether the nanoparticles could be used as a therapeutic agent capable of inhibiting tumor growth. Colorectal cancer mouse tumor models (CT26 tumor model) were used as tumor models in the experiments. $5 \times 10^6$ cells were injected into the flank of mice, and after 10 days, the tumors were visually recognized, and the mice were used for the experiments. The experiments were started by dividing the animal models into a blank group treated with PBS, a group treated with free doxorubicin (free DOX), and a group treated with doxorubicin-conjugated PEG-DNP (DOX@PEG-DNP)). The number of mice corresponding to each group was three, and each administration material was administered to the mouse tumor models via intravenous injection three times at intervals of two days. Here, the amounts of doxorubicin administered to the group treated with free doxorubicin and the group treated with doxorubicin-conjugated PEG-DNP (DOX@PEG-DNP) were 200 µg.

The size of tumors and the weight of mice in the tumor model were checked over 33 days, and the measurement results were monitored and compared. As a result, it could be confirmed that the tumor growth was most strongly inhibited and the tumor size was 3000 $mm^3$ or less in the group treated with DOX@PEG-DNP, and the above tumor size was definitely smaller than those in the other two groups. In the group treated with free doxorubicin, the tumor growth rate of only one of three mice was not inhibited and was similar to the tumor growth rate in the blank group treated with PBS, and the remaining two tumor models excluding the above tumor model surely inhibited the tumor growth rate compared with the blank group treated with PBS. In the case of the tumor models, the body weight was not rapidly reduced even in spite of the treatment with free doxorubicin or DOX@PEG-DNP. As time passed, there was a slight difference in body weight among the groups, but this was thought to be due to the difference of tumor size in the respective groups. It could be confirmed through these results that DOX@PEG-DNP did not certainly exhibit great toxicity on the tumor models compared with free doxorubicin and could inhibit tumor growth.

INDUSTRIAL APPLICABILITY

The biocompatible nanoparticles of the present invention are manufactured by inducing inter-molecular or intra-molecular crosslinking of a polysaccharide or a derivative thereof through an electron beam, so there is no a concern of occurrence of toxic problems in the human body due to the incorporation of an organic solvent or a crosslinking agent, and a separate purification process is not needed during the manufacturing procedure of the nanoparticles, and thus the nanoparticles can be massively produced with merely electron beam irradiation for a short time, leading to very excellent productivity. Furthermore, the nanoparticles of the present invention are very useful in that the nanoparticles can be utilized in various fields, such as a drug delivery system, a pharmaceutical composition, a contrast agent composition, or an adhesion barrier, and thus are highly industrially applicable.

The invention claimed is:

1. A method for preparing biocompatible nanoparticles, the method comprising:
   (a) adding to water, at least one material selected from the group consisting of polysaccharides, and a mixture of a polysaccharide and polyethylene glycol to prepare a 0.1% (w/v) to 15% (w/v) solution; and
   (b) irradiating the solution prepared in step (a) with an electron beam at a dose of 5 to 250 kGy to crosslink the material, wherein the biocompatible nanoparticle is formed exclusively by inter-molecular or intra-molecular crosslinking of at least one selected from the group consisting of a polysaccharide, and a mixture of a polysaccharide and polyethylene glycol,
   wherein the method excludes the use of a crosslinking agent, a curing agent, an inorganic material, and an organic solvent,
   wherein the polysaccharide is at least one selected from the group consisting of mannan, α-cyclodextrin, β-cyclodextrin, γ-cyclodextrin, fructo-oligosaccharides, isomalto-oligosaccharides, inulin, glycogen, amylose, carboxymethyl dextran, beta-glucan, fucoidan, and chondroitin,
   wherein a size of the nanoparticle is in a range of 1 to 700 nm.

* * * * *